US011808771B2

(12) United States Patent
Hill

(10) Patent No.: US 11,808,771 B2
(45) Date of Patent: Nov. 7, 2023

(54) METHODS AND SYSTEMS FOR SELECTIVE QUANTITATION AND DETECTION OF ALLERGENS INCLUDING GLY M 7

(71) Applicant: CORTEVA AGRISCIENCE LLC, Indianapolis, IN (US)

(72) Inventor: Ryan Hill, Zionsville, IN (US)

(73) Assignee: CORTEVA AGRISCIENCE LLC

( * ) Notice: Subject to any disclaimer, the term of this patent is extended or adjusted under 35 U.S.C. 154(b) by 1091 days.

(21) Appl. No.: 16/480,737

(22) PCT Filed: Jan. 23, 2018

(86) PCT No.: PCT/US2018/014765
§ 371 (c)(1),
(2) Date: Jul. 25, 2019

(87) PCT Pub. No.: WO2018/140370
PCT Pub. Date: Aug. 2, 2018

(65) Prior Publication Data
US 2019/0391161 A1 Dec. 26, 2019

Related U.S. Application Data

(60) Provisional application No. 62/450,246, filed on Jan. 25, 2017.

(51) Int. Cl.
*G16B 30/10* (2019.01)
*G01N 33/68* (2006.01)
*G01N 30/72* (2006.01)
*G01N 33/00* (2006.01)

(52) U.S. Cl.
CPC ..... *G01N 33/6878* (2013.01); *G01N 30/7233* (2013.01); *G01N 33/6848* (2013.01); *G16B 30/10* (2019.02); *G01N 33/0098* (2013.01)

(58) Field of Classification Search
CPC .................................. G01N 33/6878

USPC ......................................................... 436/171
See application file for complete search history.

(56) References Cited

U.S. PATENT DOCUMENTS

2015/0355189 A1\* 12/2015 Oman .................... B01D 15/08
506/2

FOREIGN PATENT DOCUMENTS

WO   WO2016025516 A1   2/2016

OTHER PUBLICATIONS

Julka et al (Anal Chem, 2012, 84: 10019-10030).*
Grebe et al (Trends in Analytical Chemistry, 2016, 84: 131-143).*
Agger et al (Clin Chem, 2010, 56(12): 1804-1813).*
International Preliminary Report on Patentability dated Jul. 30, 2019 for PCT/US2018/014765.
International Search Report dated May 15, 2018 for PCT/ US2018/014765.
Riascos, J., et al. "The seed biotinylated protein of soybean (Glycine max): a boiling-resistant new allergen (Gly m 7) with the capacity to induce IgE-mediated allergic responses." Journal of agricultural and food chemistry 64.19 (2016): 3890-3900.

\* cited by examiner

*Primary Examiner* — Sean E Aeder

(57) ABSTRACT

The invention relates to methods and systems taking advantage of bioinformatic investigations to identify candidate signature peptides for quantitative multiplex analysis of complex protein samples from plants, plant parts, and/or food products using mass spectroscopy. Provided are use and methods for selecting candidate signature peptides for quantitation using a bioinformatic approach. Also provided are systems comprising a chromatography and mass spectrometry for using selected signature peptides.

9 Claims, 9 Drawing Sheets

Specification includes a Sequence Listing.

AAELASMSAGAVK

AMGDIGGR

DTPQGSIEALQAGER (+2)

DTPQGSIEALQAGER (+3)

DYTLQAAEK

GLAASAGETAK

QSWLETR

SAAGYAAK

SAGGTTASYVGEK

SAWEQISNYSDQATQGVK

SLTSIGEK

TTAVITCTLEK

VAADLR

```
C6K8D1    1  MASEQLARRENTTTEKEIHVEKHRVPKMATHFEHLAEQAKESDITAGKDTPQGSIEALQA   60
I1M3M9    1  MASEQLARRENTTTEKEIHVEKHRVPKMATHFEHLAEQAKESDITAGKDTPQGSIEALQA   60
Q39846    1  MASEQLARRENTTTEKEIHVEKHRVPKMATHFEHLAEQAKESDITAGKDTPQGSIEALQA   60
K7LW58    1  ------------------------------MATQFEH------------LGKDTPQGSIEALQV   22

C6K8D1   61  GERVKDHAGKAMGDIGGRGKARETHELGAHFESLADKVTDHAAANVVGNKESQREARGGV  120
I1M3M9   61  GERVKDHAGKAMGDIGGRGKARETHELGAHFESLADKVTDHAAANVVGNKESQREARGGV  120
Q39846   61  GERVKDHAGKAMGDIGGRGKARETHELGAHFESLADKVTDHAAANVVGNKESQREARGGV  120
K7LW58   23  --------------------RETHELGAHFESLADKA---------PNVVGNKDNEIEARGGV   60

C6K8D1  121  RDVGKFEMRTEGGEKGNKDRPELKTRTREVIGRTEKERGRESGGQVVAEKGRETETARGR  180
I1M3M9  121  RDVGKFEMRTEGGEKGNKDRPELKTRTREVIGRTEKERGRESGGQVVAEKGRETETARGR  180
Q39846  121  RDVGKFEMRTEGGEKGNKDRPELKTRTREVIGRTEKERGRESGGQVVAEKGRETETARGR  180
K7LW58   61  ----------------GNKDRQELEKRTREVIGREEKKKGRESGGQVVAEKG------RGR  108

C6K8D1  181  VGAENEGARTTAVITCTLEKGGTQKPIREEERESESERSAWEQISNYSDQATQGVKEKY   240
I1M3M9  181  VGAENEGARTTAVITCTLEKGGTQKPIREEERESESERSAWEQISNYSDQATQGVKEKY   240
Q39846  181  VGAENEGARTTAVITCTLEKGGTQKPIREEERESESERSAWEQISNYSDQATQGVKEKY   240
K7LW58  109  VGPENEGARTTAVITCTLEKGGATQKPLREEESES-TERSTWEQISNYSDQATQGVKERY   167

C6K8D1  241  ERAKQAASETLNTTTQTAQEKSAQAKNLAAQAKDATLEKGQQGYAVTKDTISSAAKTASE  300
I1M3M9  241  ERAKQAASETLNTTTQTAQEKSAQAKNLAAQAKDATLEKGQQGYAVTKDTISSAAKTASE  300
Q39846  241  ERAKQAASETLNTTTQTAQEKSAQAKNLAAQAKDATLEKGQQGYAVTKDTISSAAKTASE  300
K7LW58  168  DRAKQAASETLNTTAETAQEKSAQAKDLATQAKDATLEKGQQGYVATKDTISSAAKTASE  227

C6K8D1  301  KTAPVAEKAKDYTLQAAEKAKSAGGTTASYVGEKAVQAKDVAVESGKSAAGYAAKVAADL  360
I1M3M9  301  KTAPVAEKAKDYTLQAAEKAKSAGGTTASYVGEKAVQAKDVAVESGKSAAGYAAKVAADL  360
Q39846  301  KTAPVAEKAKDYTLQAAEKAKSAGGTTASYVGEKAVQAKDVAVESGKSAAGYAAKVAADL  360
K7LW58  228  KTAPVAEKAKEYTLQAAEKTKSVGGTTASYVGEKAVQAKDVTVESGKNAAGYAAKVAVDL  287

C6K8D1  361  RDKATAVGWAAAHFSAEKTVEGTKAAAHVVEGAAGYAGHKAAELASMSAGAVKGLAASAG  420
I1M3M9  361  RDKATAVGWAAAHFSAEKTVEGTKAAAHVVEGAAGYAGHKAAELASMSAGAVKGLAASAG  420
Q39846  361  RDKATAVGWAAAHFSAEKTVEGTKAAAHVVEGAAGYAGHKAAELASMSAGAVKGLAASAG  420
K7LW58  288  KDKAASVGWAAAHFSAEKTVEGTKAAAHVVEGAAGYAGHKAAELASMTGAVKGLAASAG  347

C6K8D1  421  ETAKEYTAKKKEEAQRELEAKKPSQPQEAEERPSEGIGETVRQYAQKPKPSERNPQKEGT  480
I1M3M9  421  ETAKEYTAKKKEEAQRELEAKKPSQPQEAEERPSEGIGETVRQYAQKPKPSERNPQKEGT  480
Q39846  421  ETAKEYTAKKKEEAQRELEAKKPSQPQEAEERPSEGIGETVRQYAQKPKPSEGNPQKEGT  480
K7LW58  348  ETAKEYTTRKKEEAQRELEAKKAFQPQEAEERPSQGIGETV-------------------  388

C6K8D1  481  GSIVFTAIGETVSSAGEKVKKPFKNTTGGE-----------SEGGGGKEEGKSVIGKSLTS  530
I1M3M9  481  GSIVFTAIGETVSSAGEKVKKPFKNMGGE----------SEGGGGKEEGKSVIGKSLTS  530
Q39846  481  GSIVFTAIGETVSSAGEKVKKPFKNMGGE----------SEGGGGKEEGKSVIGKSLTS  530
K7LW58  389  -------------SSVGEKVKKPFENILGGEGKKDESGGNDQSSGGGQEQGKSIIGQTLTS  436

C6K8D1  481  IGEKLGDAKQREELLDNVTGNITEGGGEVLGAVGETVAEIGQNMMKPAEIVQERAHVRQA  590
I1M3M9  481  IGEKLGDAKQREELLDNVTGNITEGGGEVLGAVGETVAEIGQNMMKPAEIVQERAHVRQA  590
Q39846  481  IGEKLGDAKQREELLDNVTGNITEGGGEVLGAVGETVAEIGQNMMKPAEIVQERAHVRQA  590
K7LW58  437  IGEKLGDAKQREELIDNV----TEGGSEVLGAVGETVGEIGQNTMKPAEIVQERAHVRQE  492

C6K8D1  591  GGVLDAIGETIAEIAETTRVMVSGEDERVLRQSVVLETRVTGRAKHEEGSHGA         643
I1M3M9  591  GGVLDAIGETIAEIAETTRVMVSGEDERVLRQSVVLETRVTGRAKHEEGSHGA         643
Q39846  591  GGVLDAIGETIAEIAETTRVMVSGEDERVLRQSVVLETRVTGRAKHEEGSHGA         643
K7LW58  493  GGVLDAIGETIAEIAETTRVMVAGEDKRVMPE-----TRVTDRAKHEERSESA         540
```

FIG. 14

SEQUENCE LISTING

```
<160> NUMBER OF SEQ ID NOS: 43

<210> SEQ ID NO 1
<211> LENGTH: 10
<212> TYPE: PRT
<213> ORGANISM: Glycine max

<400> SEQUENCE: 1

Ser Tyr Pro Ser Asn Ala Thr Cys Pro Arg
1               5                   10

<210> SEQ ID NO 2
<211> LENGTH: 13
<212> TYPE: PRT
<213> ORGANISM: Glycine max

<400> SEQUENCE: 2

Tyr Met Val Ile Gln Gly Glu Pro Gly Ala Val Ile Arg
1               5                   10

<210> SEQ ID NO 3
<211> LENGTH: 10
<212> TYPE: PRT
<213> ORGANISM: Glycine max

<400> SEQUENCE: 3

Asn Ile Leu Glu Ala Ser Tyr Asp Thr Lys
1               5                   10

<210> SEQ ID NO 4
<211> LENGTH: 7
<212> TYPE: PRT
<213> ORGANISM: Glycine max

<400> SEQUENCE: 4
```

Val Thr Ala Pro Ala Met Arg
1               5

<210> SEQ ID NO 5
<211> LENGTH: 12
<212> TYPE: PRT
<213> ORGANISM: Glycine max

<400> SEQUENCE: 5

Asn Asn Asn Pro Phe Ser Phe Leu Val Pro Pro Lys
1               5                   10

<210> SEQ ID NO 6
<211> LENGTH: 7
<212> TYPE: PRT
<213> ORGANISM: Glycine max

<400> SEQUENCE: 6

Ala Asp Phe Tyr Asn Pro Lys
1               5

<210> SEQ ID NO 7
<211> LENGTH: 11
<212> TYPE: PRT
<213> ORGANISM: Glycine max

<400> SEQUENCE: 7

Gly Gly Gly Ile Glu Val Asp Ser Thr Gly Lys
1               5                   10

<210> SEQ ID NO 8
<211> LENGTH: 11
<212> TYPE: PRT
<213> ORGANISM: Glycine max

<400> SEQUENCE: 8

Gly Ile Gly Thr Ile Ile Ser Ser Pro Tyr Arg
1               5                   10

<210> SEQ ID NO 9
<211> LENGTH: 14
<212> TYPE: PRT
<213> ORGANISM: Glycine max

<400> SEQUENCE: 9

Asn Lys Pro Gln Phe Leu Ala Gly Ala Ala Ser Leu Leu Arg
1               5                   10

<210> SEQ ID NO 10
<211> LENGTH: 7
<212> TYPE: PRT
<213> ORGANISM: Glycine max

<400> SEQUENCE: 10

Gly Val Ile Thr Gln Val Lys
1               5

<210> SEQ ID NO 11
<211> LENGTH: 12
<212> TYPE: PRT
<213> ORGANISM: Glycine max

<400> SEQUENCE: 11

Ile Met Glu Asn Gln Ser Glu Glu Leu Glu Glu Lys

-continued

<210> SEQ ID NO 12
<211> LENGTH: 643
<212> TYPE: PRT
<213> ORGANISM: Glycine max

<400> SEQUENCE: 12

```
Met Ala Ser Glu Gln Leu Ala Arg Arg Glu Asn Thr Thr Thr Glu Lys
1               5                   10                  15

Glu Ile His Val Glu Lys His Arg Val Pro Lys Met Ala Thr His Phe
            20                  25                  30

Glu His Leu Ala Glu Gln Ala Lys Glu Ser Asp Ile Thr Ala Gly Lys
        35                  40                  45

Asp Thr Pro Gln Gly Ser Ile Glu Ala Leu Gln Ala Gly Glu Arg Val
    50                  55                  60

Lys Asp His Ala Gly Lys Ala Met Gly Asp Ile Gly Gly Arg Gly Lys
65                  70                  75                  80

Ala Arg Glu Thr His Glu Leu Gly Ala His Phe Glu Ser Leu Ala Asp
                85                  90                  95

Lys Val Thr Asp His Ala Ala Asn Val Val Gly Asn Lys Glu Ser
            100                 105                 110

Gln Arg Glu Ala Arg Gly Gly Val Arg Asp Val Gly Lys Phe Glu Met
        115                 120                 125

Arg Thr Glu Gly Gly Glu Lys Gly Asn Lys Asp Arg Pro Glu Leu Lys
    130                 135                 140

Thr Arg Thr Arg Glu Val Ile Gly Arg Thr Glu Lys Glu Arg Gly Arg
145                 150                 155                 160

Glu Ser Gly Gly Gln Val Val Ala Glu Lys Gly Arg Glu Thr Glu Thr
                165                 170                 175

Ala Arg Gly Arg Val Gly Ala Glu Asn Glu Gly Ala Arg Thr Thr Ala
            180                 185                 190

Val Ile Thr Cys Thr Leu Glu Lys Gly Gly Gly Thr Gln Lys Pro Ile
        195                 200                 205

Arg Glu Glu Glu Arg Glu Ser Glu Ser Glu Arg Ser Ala Trp Glu Gln
    210                 215                 220

Ile Ser Asn Tyr Ser Asp Gln Ala Thr Gln Gly Val Lys Glu Lys Tyr
225                 230                 235                 240

Glu Arg Ala Lys Gln Ala Ala Ser Glu Thr Leu Asn Thr Thr Thr Gln
                245                 250                 255

Thr Ala Gln Glu Lys Ser Ala Gln Ala Lys Asn Leu Ala Ala Gln Ala
            260                 265                 270

Lys Asp Ala Thr Leu Glu Lys Gly Gln Gln Gly Tyr Ala Val Thr Lys
        275                 280                 285

Asp Thr Ile Ser Ser Ala Ala Lys Thr Ala Ser Glu Lys Thr Ala Pro
    290                 295                 300

Val Ala Glu Lys Ala Lys Asp Tyr Thr Leu Gln Ala Ala Glu Lys Ala
305                 310                 315                 320

Lys Ser Ala Gly Gly Thr Thr Ala Ser Tyr Val Gly Glu Lys Ala Val
                325                 330                 335

Gln Ala Lys Asp Val Ala Val Glu Ser Gly Lys Ser Ala Ala Gly Tyr
            340                 345                 350

Ala Ala Lys Val Ala Ala Asp Leu Arg Asp Lys Ala Thr Ala Val Gly
        355                 360                 365
```

-continued

Trp Ala Ala Ala His Phe Ser Ala Glu Lys Thr Val Glu Gly Thr Lys
370                 375                 380

Ala Ala Ala His Val Val Glu Gly Ala Ala Gly Tyr Ala Gly His Lys
385                 390                 395                 400

Ala Ala Glu Leu Ala Ser Met Ser Ala Gly Ala Val Lys Gly Leu Ala
            405                 410                 415

Ala Ser Ala Gly Glu Thr Ala Lys Glu Tyr Thr Ala Lys Lys Lys Glu
            420                 425                 430

Glu Ala Gln Arg Glu Leu Glu Ala Lys Lys Pro Ser Gln Pro Gln Glu
            435                 440                 445

Ala Glu Glu Arg Pro Ser Glu Gly Ile Gly Glu Thr Val Arg Gln Tyr
450                 455                 460

Ala Gln Lys Pro Lys Pro Ser Glu Arg Asn Pro Gln Lys Glu Gly Thr
465                 470                 475                 480

Gly Ser Ile Val Phe Thr Ala Ile Gly Glu Thr Val Ser Ser Ala Gly
                485                 490                 495

Glu Lys Val Lys Lys Pro Phe Lys Asn Thr Thr Gly Gly Glu Ser Glu
                500                 505                 510

Gly Gly Gly Gly Lys Glu Glu Gly Lys Ser Val Ile Gly Lys Ser Leu
            515                 520                 525

Thr Ser Ile Gly Glu Lys Leu Gly Asp Ala Lys Gln Arg Glu Glu Leu
530                 535                 540

Leu Asp Asn Val Thr Gly Asn Ile Thr Glu Gly Gly Glu Val Leu
545                 550                 555                 560

Gly Ala Val Gly Glu Thr Val Ala Glu Ile Gly Gln Asn Met Met Lys
                565                 570                 575

Pro Ala Glu Ile Val Gln Glu Arg Ala His Val Arg Gln Ala Gly Gly
                580                 585                 590

Val Leu Asp Ala Ile Gly Glu Thr Ile Ala Glu Ile Ala Glu Thr Thr
            595                 600                 605

Arg Val Met Val Ser Gly Glu Asp Glu Arg Val Leu Arg Gln Ser Val
            610                 615                 620

Val Leu Glu Thr Arg Val Thr Gly Arg Ala Lys His Glu Glu Gly Ser
625                 630                 635                 640

His Gly Ala

<210> SEQ ID NO 13
<211> LENGTH: 643
<212> TYPE: PRT
<213> ORGANISM: Glycine max

<400> SEQUENCE: 13

Met Ala Ser Glu Gln Leu Ala Arg Arg Glu Asn Thr Thr Thr Glu Lys
1               5                   10                  15

Glu Ile His Val Glu Lys His Arg Val Pro Lys Met Ala Thr His Phe
                20                  25                  30

Glu His Leu Ala Glu Gln Ala Lys Glu Ser Asp Ile Thr Ala Gly Lys
            35                  40                  45

Asp Thr Pro Gln Gly Ser Ile Glu Ala Leu Gln Ala Gly Glu Arg Val
        50                  55                  60

Lys Asp His Ala Gly Lys Ala Met Gly Asp Ile Gly Gly Arg Gly Lys
65                  70                  75                  80

Ala Arg Glu Thr His Glu Leu Gly Ala His Phe Glu Ser Leu Ala Asp
                85                  90                  95

-continued

```
Lys Val Thr Asp His Ala Ala Asn Val Val Gly Asn Lys Glu Ser
            100                 105                 110
Gln Arg Glu Ala Arg Gly Gly Val Arg Asp Val Gly Lys Phe Glu Met
        115                 120                 125
Arg Thr Glu Gly Gly Glu Lys Gly Asn Lys Asp Arg Pro Glu Leu Lys
    130                 135                 140
Thr Arg Thr Arg Glu Val Ile Gly Arg Thr Glu Lys Glu Arg Gly Arg
145                 150                 155                 160
Glu Ser Gly Gly Gln Val Val Ala Glu Lys Gly Arg Glu Thr Glu Thr
                165                 170                 175
Ala Arg Gly Arg Val Gly Ala Glu Asn Glu Gly Ala Arg Thr Thr Ala
            180                 185                 190
Val Ile Thr Cys Thr Leu Glu Lys Gly Gly Thr Gln Lys Pro Ile
        195                 200                 205
Arg Glu Glu Arg Glu Ser Glu Ser Glu Arg Ser Ala Trp Glu Gln
    210                 215                 220
Ile Ser Asn Tyr Ser Asp Gln Ala Thr Gln Gly Val Lys Glu Lys Tyr
225                 230                 235                 240
Glu Arg Ala Lys Gln Ala Ala Ser Glu Thr Leu Asn Thr Thr Thr Gln
                245                 250                 255
Thr Ala Gln Glu Lys Ser Ala Gln Ala Lys Asn Leu Ala Ala Gln Ala
            260                 265                 270
Lys Asp Ala Thr Leu Glu Lys Gly Gln Gln Gly Tyr Ala Val Thr Lys
        275                 280                 285
Asp Thr Ile Ser Ser Ala Ala Lys Thr Ala Ser Glu Lys Thr Ala Pro
290                 295                 300
Val Ala Glu Lys Ala Lys Asp Tyr Thr Leu Gln Ala Ala Glu Lys Ala
305                 310                 315                 320
Lys Ser Ala Gly Gly Thr Thr Ala Ser Tyr Val Gly Glu Lys Ala Val
                325                 330                 335
Gln Ala Lys Asp Val Ala Val Glu Ser Gly Lys Ser Ala Ala Gly Tyr
            340                 345                 350
Ala Ala Lys Val Ala Ala Asp Leu Arg Asp Lys Ala Thr Ala Val Gly
        355                 360                 365
Trp Ala Ala His Phe Ser Ala Glu Lys Thr Val Glu Gly Thr Lys
    370                 375                 380
Ala Ala Ala His Val Val Glu Gly Ala Ala Gly Tyr Ala Gly His Lys
385                 390                 395                 400
Ala Ala Glu Leu Ala Ser Met Ser Ala Gly Ala Val Lys Gly Leu Ala
                405                 410                 415
Ala Ser Ala Gly Glu Thr Ala Lys Glu Tyr Thr Ala Lys Lys Lys Glu
            420                 425                 430
Glu Ala Gln Arg Glu Leu Glu Ala Lys Lys Pro Ser Gln Pro Gln Glu
        435                 440                 445
Ala Glu Glu Arg Pro Ser Glu Gly Ile Gly Glu Thr Val Arg Gln Tyr
    450                 455                 460
Ala Gln Lys Pro Lys Pro Ser Glu Arg Asn Pro Gln Lys Glu Gly Thr
465                 470                 475                 480
Gly Ser Ile Val Phe Thr Ala Ile Gly Glu Thr Val Ser Ala Gly
                485                 490                 495
Glu Lys Val Lys Lys Pro Phe Lys Asn Thr Met Gly Gly Glu Ser Glu
            500                 505                 510
Gly Gly Gly Gly Lys Glu Glu Gly Lys Ser Val Ile Gly Lys Ser Leu
```

```
                515                 520                 525
Thr Ser Ile Gly Glu Lys Leu Gly Asp Ala Lys Gln Arg Glu Glu Leu
        530                 535                 540

Leu Asp Asn Val Thr Gly Asn Ile Thr Glu Gly Gly Glu Val Leu
545                 550                 555                 560

Gly Ala Val Gly Glu Thr Val Ala Glu Ile Gly Gln Asn Met Met Lys
                565                 570                 575

Pro Ala Glu Ile Val Gln Glu Arg Ala His Val Arg Gln Ala Gly Gly
            580                 585                 590

Val Leu Asp Ala Ile Gly Glu Thr Ile Ala Glu Ile Ala Glu Thr Thr
        595                 600                 605

Arg Val Met Val Ser Gly Glu Asp Glu Arg Val Leu Arg Gln Ser Val
    610                 615                 620

Val Leu Glu Thr Arg Val Thr Gly Arg Ala Lys His Glu Glu Gly Ser
625                 630                 635                 640

His Gly Ala

<210> SEQ ID NO 14
<211> LENGTH: 643
<212> TYPE: PRT
<213> ORGANISM: Glycine max

<400> SEQUENCE: 14

Met Ala Ser Glu Gln Leu Ala Arg Arg Glu Asn Thr Thr Thr Glu Lys
1               5                   10                  15

Glu Ile His Val Glu Lys His Arg Val Pro Lys Met Ala Thr His Phe
            20                  25                  30

Glu His Leu Ala Glu Gln Ala Lys Glu Ser Asp Ile Thr Ala Gly Lys
        35                  40                  45

Asp Thr Pro Gln Gly Ser Ile Glu Ala Leu Gln Ala Gly Glu Arg Val
    50                  55                  60

Lys Asp His Ala Gly Lys Ala Met Gly Asp Ile Gly Gly Arg Gly Lys
65                  70                  75                  80

Ala Arg Glu Thr His Glu Leu Gly Ala His Phe Glu Ser Leu Ala Asp
                85                  90                  95

Lys Val Thr Asp His Ala Ala Ala Asn Val Val Gly Asn Lys Glu Ser
            100                 105                 110

Gln Arg Glu Ala Arg Gly Gly Val Arg Asp Val Gly Lys Phe Glu Met
        115                 120                 125

Arg Thr Glu Gly Gly Glu Lys Gly Asn Lys Asp Arg Pro Glu Leu Lys
    130                 135                 140

Thr Arg Thr Arg Glu Val Ile Gly Arg Thr Glu Lys Glu Arg Gly Arg
145                 150                 155                 160

Glu Ser Gly Gly Gln Val Val Ala Lys Gly Arg Glu Thr Glu Thr
                165                 170                 175

Ala Arg Gly Arg Val Gly Ala Glu Asn Glu Gly Ala Arg Thr Thr Ala
            180                 185                 190

Val Ile Thr Cys Thr Leu Glu Lys Gly Gly Gly Thr Gln Lys Pro Ile
        195                 200                 205

Arg Glu Glu Glu Arg Glu Ser Glu Ser Glu Arg Ser Ala Trp Glu Gln
    210                 215                 220

Ile Ser Asn Tyr Ser Asp Gln Ala Thr Gln Gly Val Lys Glu Lys Tyr
225                 230                 235                 240

Glu Arg Ala Lys Gln Ala Ala Ser Glu Thr Leu Asn Thr Thr Thr Gln
```

```
                        245                 250                 255
Thr Ala Gln Glu Lys Ser Ala Gln Ala Lys Asn Leu Ala Ala Gln Ala
                260                 265                 270
Lys Asp Ala Thr Leu Glu Lys Gly Gln Gln Gly Tyr Ala Val Thr Lys
            275                 280                 285
Asp Thr Ile Ser Ser Ala Ala Lys Thr Ala Ser Glu Lys Thr Ala Pro
        290                 295                 300
Val Ala Glu Lys Ala Lys Asp Tyr Thr Leu Gln Ala Ala Glu Lys Ala
305                 310                 315                 320
Lys Ser Ala Gly Gly Thr Thr Ala Ser Tyr Val Gly Glu Lys Ala Val
                325                 330                 335
Gln Ala Lys Asp Val Ala Val Glu Ser Gly Lys Ser Ala Ala Gly Tyr
            340                 345                 350
Ala Ala Lys Val Ala Ala Asp Leu Arg Asp Lys Ala Thr Ala Val Gly
        355                 360                 365
Trp Ala Ala Ala His Phe Ser Ala Glu Lys Thr Val Glu Gly Thr Lys
    370                 375                 380
Ala Ala Ala His Val Val Glu Gly Ala Ala Gly Tyr Ala Gly His Lys
385                 390                 395                 400
Ala Ala Glu Leu Ala Ser Met Ser Ala Gly Ala Val Lys Gly Leu Ala
                405                 410                 415
Ala Ser Ala Gly Glu Thr Ala Lys Glu Tyr Thr Ala Lys Lys Lys Glu
            420                 425                 430
Glu Ala Gln Arg Glu Leu Glu Ala Lys Lys Pro Ser Gln Pro Gln Glu
        435                 440                 445
Ala Glu Glu Arg Pro Ser Glu Gly Ile Gly Glu Thr Val Arg Gln Tyr
    450                 455                 460
Ala Gln Lys Pro Lys Pro Ser Glu Gly Asn Pro Gln Lys Glu Gly Thr
465                 470                 475                 480
Gly Ser Ile Val Phe Thr Ala Ile Gly Glu Thr Val Ser Ser Ala Gly
                485                 490                 495
Glu Lys Val Lys Lys Pro Phe Lys Asn Thr Met Gly Gly Glu Ser Glu
            500                 505                 510
Gly Gly Gly Gly Lys Glu Gly Lys Ser Val Ile Gly Lys Ser Leu
        515                 520                 525
Thr Ser Ile Gly Glu Lys Leu Gly Asp Ala Lys Gln Arg Glu Glu Leu
    530                 535                 540
Leu Asp Asn Val Thr Gly Asn Ile Thr Glu Gly Gly Glu Val Leu
545                 550                 555                 560
Gly Ala Val Gly Glu Thr Val Ala Glu Ile Gly Gln Asn Met Met Lys
                565                 570                 575
Pro Ala Glu Ile Val Gln Glu Arg Ala His Val Arg Gln Ala Gly Gly
            580                 585                 590
Val Leu Asp Ala Ile Gly Glu Thr Ile Ala Glu Ile Ala Glu Thr Thr
        595                 600                 605
Arg Val Met Val Ser Gly Glu Asp Glu Arg Val Leu Arg Gln Ser Val
    610                 615                 620
Val Leu Glu Thr Arg Val Thr Gly Arg Ala Lys His Glu Glu Gly Ser
625                 630                 635                 640
His Gly Ala

<210> SEQ ID NO 15
<211> LENGTH: 540
```

```
<212> TYPE: PRT
<213> ORGANISM: Glycine max

<400> SEQUENCE: 15

Met Ala Thr Gln Phe Glu His Leu Gly Lys Asp Thr Pro Gln Gly Ser
1               5                   10                  15

Ile Glu Ala Leu Gln Val Gly Glu Arg Val Arg Glu Thr His Glu Leu
            20                  25                  30

Gly Ala His Phe Glu Ser Leu Ala Asp Lys Ala Pro Asn Val Val Gly
        35                  40                  45

Asn Lys Asp Asn Glu Ile Glu Ala Arg Gly Gly Val Arg Asp Val Gly
    50                  55                  60

Lys Phe Glu Met Lys Gly Asn Lys Asp Arg Gln Glu Leu Glu Lys Arg
65                  70                  75                  80

Thr Arg Glu Val Ile Gly Arg Glu Glu Lys Lys Gly Arg Glu Ser
                85                  90                  95

Gly Gly Gln Val Val Ala Glu Lys Gly Arg Gly Arg Val Gly Pro Glu
            100                 105                 110

Asn Glu Gly Ala Arg Thr Thr Ala Val Ile Thr Cys Thr Leu Glu Lys
        115                 120                 125

Gly Gly Ala Thr Gln Lys Pro Leu Arg Glu Glu Ser Glu Ser Thr
    130                 135                 140

Glu Arg Ser Thr Trp Glu Gln Ile Ser Asn Tyr Ser Asp Gln Ala Thr
145                 150                 155                 160

Gln Gly Val Lys Glu Arg Tyr Asp Arg Ala Lys Gln Ala Ala Ser Glu
                165                 170                 175

Thr Leu Asn Thr Thr Ala Glu Thr Ala Gln Glu Lys Ser Ala Gln Ala
            180                 185                 190

Lys Asp Leu Ala Thr Gln Ala Lys Asp Ala Thr Leu Glu Lys Gly Gln
        195                 200                 205

Gln Gly Tyr Val Ala Thr Lys Asp Thr Ile Ser Ser Ala Ala Lys Thr
    210                 215                 220

Ala Ser Glu Lys Thr Ala Pro Val Ala Glu Lys Ala Lys Glu Tyr Thr
225                 230                 235                 240

Leu Gln Ala Ala Glu Lys Thr Lys Ser Val Gly Gly Thr Thr Ala Ser
                245                 250                 255

Tyr Val Gly Glu Lys Ala Val Gln Ala Lys Asp Val Thr Val Glu Ser
            260                 265                 270

Gly Lys Asn Ala Ala Gly Tyr Ala Ala Lys Val Ala Val Asp Leu Lys
        275                 280                 285

Asp Lys Ala Ala Ser Val Gly Trp Ala Ala Ala His Phe Ser Ala Glu
    290                 295                 300

Lys Thr Val Glu Gly Thr Lys Ala Ala Ala His Val Val Glu Gly Ala
305                 310                 315                 320

Ala Gly Tyr Ala Gly His Lys Ala Ala Glu Leu Ala Ser Met Ser Thr
                325                 330                 335

Gly Ala Val Lys Gly Leu Ala Ala Ser Ala Gly Glu Thr Ala Lys Glu
            340                 345                 350

Tyr Thr Thr Arg Lys Lys Glu Glu Ala Gln Arg Glu Leu Glu Ala Lys
        355                 360                 365

Lys Ala Phe Gln Pro Gln Glu Ala Glu Arg Pro Ser Gln Gly Ile
    370                 375                 380

Gly Glu Thr Val Ser Ser Val Gly Glu Lys Val Lys Lys Pro Phe Glu
385                 390                 395                 400
```

```
Asn Ile Leu Gly Gly Glu Gly Lys Lys Asp Glu Ser Gly Asn Asp
            405                 410                 415

Gln Ser Ser Gly Gly Gln Glu Gln Gly Lys Ser Ile Ile Gly Gln
            420                 425                 430

Thr Leu Thr Ser Ile Gly Glu Lys Leu Gly Asp Ala Lys Gln Arg Glu
            435                 440                 445

Glu Leu Ile Asp Asn Val Thr Glu Gly Gly Ser Glu Val Leu Gly Ala
            450                 455                 460

Val Gly Glu Thr Val Gly Glu Ile Gly Gln Asn Thr Met Lys Pro Ala
465                 470                 475                 480

Glu Ile Val Gln Glu Arg Ala His Val Arg Gln Glu Gly Gly Val Leu
            485                 490                 495

Asp Ala Ile Gly Glu Thr Ile Ala Glu Ile Ala Glu Thr Thr Arg Val
            500                 505                 510

Met Val Ala Gly Glu Asp Lys Arg Val Met Pro Glu Thr Arg Val Thr
            515                 520                 525

Asp Arg Ala Lys His Glu Glu Arg Ser Glu Ser Ala
            530                 535                 540

<210> SEQ ID NO 16
<211> LENGTH: 119
<212> TYPE: PRT
<213> ORGANISM: Glycine max

<400> SEQUENCE: 16

Met Gly Ser Lys Val Val Ala Ser Val Ala Leu Leu Leu Ser Ile Asn
1               5                   10                  15

Ile Leu Phe Ile Ser Met Val Ser Ser Ser His Tyr Asp Pro Gln
            20                  25                  30

Pro Gln Pro Ser His Val Thr Ala Leu Ile Thr Arg Pro Ser Cys Pro
            35                  40                  45

Asp Leu Ser Ile Cys Leu Asn Ile Leu Gly Gly Ser Leu Gly Thr Val
        50                  55                  60

Asp Asp Cys Cys Ala Leu Ile Gly Gly Leu Gly Asp Ile Glu Ala Ile
65                  70                  75                  80

Val Cys Leu Cys Ile Gln Leu Arg Ala Leu Gly Ile Leu Asn Leu Asn
            85                  90                  95

Arg Asn Leu Gln Leu Ile Leu Asn Ser Cys Gly Arg Ser Tyr Pro Ser
            100                 105                 110

Asn Ala Thr Cys Pro Arg Thr
        115

<210> SEQ ID NO 17
<211> LENGTH: 131
<212> TYPE: PRT
<213> ORGANISM: Glycine max

<400> SEQUENCE: 17

Met Ser Trp Gln Ala Tyr Val Asp Asp His Leu Leu Cys Gly Ile Glu
1               5                   10                  15

Gly Asn His Leu Thr His Ala Ala Ile Ile Gly Gln Asp Gly Ser Val
            20                  25                  30

Trp Leu Gln Ser Thr Asp Phe Pro Gln Phe Lys Pro Glu Glu Ile Thr
            35                  40                  45

Ala Ile Met Asn Asp Phe Asn Glu Pro Gly Ser Leu Ala Pro Thr Gly
        50                  55                  60
```

Leu Tyr Leu Gly Gly Thr Lys Tyr Met Val Ile Gln Gly Glu Pro Gly
65                  70                  75                  80

Ala Val Ile Arg Gly Lys Lys Gly Pro Gly Val Thr Val Lys Lys
                85                  90                  95

Thr Gly Ala Ala Leu Ile Ile Gly Ile Tyr Asp Glu Pro Met Thr Pro
            100                 105                 110

Gly Gln Cys Asn Met Val Val Glu Arg Leu Gly Asp Tyr Leu Ile Asp
        115                 120                 125

Gln Gly Tyr
    130

<210> SEQ ID NO 18
<211> LENGTH: 158
<212> TYPE: PRT
<213> ORGANISM: Glycine max

<400> SEQUENCE: 18

Met Gly Val Phe Thr Phe Glu Asp Glu Ile Asn Ser Pro Val Ala Pro
1               5                   10                  15

Ala Thr Leu Tyr Lys Ala Leu Val Thr Asp Ala Asp Asn Val Ile Pro
            20                  25                  30

Lys Ala Leu Asp Ser Phe Lys Ser Val Glu Asn Val Glu Gly Asn Gly
        35                  40                  45

Gly Pro Gly Thr Ile Lys Lys Ile Thr Phe Leu Asp Gly Glu Thr
    50                  55                  60

Lys Phe Val Leu His Lys Ile Glu Ser Ile Asp Glu Ala Asn Leu Gly
65                  70                  75                  80

Tyr Ser Tyr Ser Val Val Gly Gly Ala Ala Leu Pro Asp Thr Ala Glu
                85                  90                  95

Lys Ile Thr Phe Asp Ser Lys Leu Val Ala Gly Pro Asn Gly Gly Ser
            100                 105                 110

Ala Gly Lys Leu Thr Val Lys Tyr Glu Thr Lys Gly Asp Ala Glu Pro
        115                 120                 125

Asn Gln Asp Glu Leu Lys Thr Gly Lys Ala Lys Ala Asp Ala Leu Phe
    130                 135                 140

Lys Ala Ile Glu Ala Tyr Leu Leu Ala His Pro Asp Tyr Asn
145                 150                 155

<210> SEQ ID NO 19
<211> LENGTH: 605
<212> TYPE: PRT
<213> ORGANISM: Glycine max

<400> SEQUENCE: 19

Met Met Arg Ala Arg Phe Pro Leu Leu Leu Gly Leu Val Phe Leu
1               5                   10                  15

Ala Ser Val Ser Val Ser Phe Gly Ile Ala Tyr Trp Glu Lys Glu Asn
            20                  25                  30

Pro Lys His Asn Lys Cys Leu Gln Ser Cys Asn Ser Glu Arg Asp Ser
        35                  40                  45

Tyr Arg Asn Gln Ala Cys His Ala Arg Cys Asn Leu Leu Lys Val Glu
    50                  55                  60

Lys Glu Glu Cys Glu Glu Gly Glu Ile Pro Arg Pro Arg Pro Arg Pro
65                  70                  75                  80

Gln His Pro Glu Arg Glu Pro Gln Gln Pro Gly Glu Lys Glu Glu Asp
                85                  90                  95

Glu Asp Glu Gln Pro Arg Pro Ile Pro Phe Pro Arg Pro Gln Pro Arg
            100                 105                 110

Gln Glu Glu His Glu Gln Arg Glu Glu Gln Glu Trp Pro Arg Lys
        115                 120                 125

Glu Glu Lys Arg Gly Lys Gly Ser Glu Glu Asp Glu Asp Glu
        130                 135                 140

Asp Glu Glu Gln Asp Glu Arg Gln Phe Pro Phe Pro Arg Pro Pro His
145                 150                 155                 160

Gln Lys Glu Glu Arg Asn Glu Glu Asp Glu Asp Glu Gln Gln
                165                 170                 175

Arg Glu Ser Glu Glu Ser Glu Asp Ser Glu Leu Arg Arg His Lys Asn
            180                 185                 190

Lys Asn Pro Phe Leu Phe Gly Ser Asn Arg Phe Glu Thr Leu Phe Lys
                195                 200                 205

Asn Gln Tyr Gly Arg Ile Arg Val Leu Gln Arg Phe Asn Gln Arg Ser
            210                 215                 220

Pro Gln Leu Gln Asn Leu Arg Asp Tyr Arg Ile Leu Glu Phe Asn Ser
225                 230                 235                 240

Lys Pro Asn Thr Leu Leu Pro Asn His Ala Asp Ala Asp Tyr Leu
                245                 250                 255

Ile Val Ile Leu Asn Gly Thr Ala Ile Leu Ser Leu Val Asn Asn Asp
            260                 265                 270

Asp Arg Asp Ser Tyr Arg Leu Gln Ser Gly Asp Ala Leu Arg Val Pro
            275                 280                 285

Ser Gly Thr Thr Tyr Tyr Val Val Asn Pro Asp Asn Asn Glu Asn Leu
            290                 295                 300

Arg Leu Ile Thr Leu Ala Ile Pro Val Asn Lys Pro Gly Arg Phe Glu
305                 310                 315                 320

Ser Phe Phe Leu Ser Ser Thr Glu Ala Gln Gln Ser Tyr Leu Gln Gly
                325                 330                 335

Phe Ser Arg Asn Ile Leu Glu Ala Ser Tyr Asp Thr Lys Phe Glu Glu
            340                 345                 350

Ile Asn Lys Val Leu Phe Ser Arg Glu Glu Gly Gln Gln Gln Gly Glu
            355                 360                 365

Gln Arg Leu Gln Glu Ser Val Ile Val Glu Ile Ser Lys Glu Gln Ile
            370                 375                 380

Arg Ala Leu Ser Lys Arg Ala Lys Ser Ser Arg Lys Thr Ile Ser
385                 390                 395                 400

Ser Glu Asp Lys Pro Phe Asn Leu Arg Ser Arg Asp Pro Ile Tyr Ser
                405                 410                 415

Asn Lys Leu Gly Lys Phe Phe Glu Ile Thr Pro Glu Lys Asn Pro Gln
                420                 425                 430

Leu Arg Asp Leu Asp Ile Phe Leu Ser Ile Val Asp Met Asn Glu Gly
            435                 440                 445

Ala Leu Leu Leu Pro His Phe Asn Ser Lys Ala Ile Val Ile Leu Val
                450                 455                 460

Ile Asn Glu Gly Asp Ala Asn Ile Glu Leu Val Gly Leu Lys Glu Gln
465                 470                 475                 480

Gln Gln Glu Gln Gln Gln Gln Glu Gln Pro Leu Glu Val Arg Lys Tyr
                485                 490                 495

Arg Ala Glu Leu Ser Glu Gln Asp Ile Phe Val Ile Pro Ala Gly Tyr
            500                 505                 510

```
Pro Val Val Asn Ala Thr Ser Asn Leu Asn Phe Phe Ala Ile Gly
            515                 520                 525

Ile Asn Ala Glu Asn Asn Gln Arg Asn Phe Leu Ala Gly Ser Gln Asp
    530                 535                 540

Asn Val Ile Ser Gln Ile Pro Ser Gln Val Gln Glu Leu Ala Phe Pro
545                 550                 555                 560

Gly Ser Ala Gln Ala Val Glu Lys Leu Leu Lys Asn Gln Arg Glu Ser
            565                 570                 575

Tyr Phe Val Asp Ala Gln Pro Lys Lys Glu Glu Gly Asn Lys Gly
            580                 585                 590

Arg Lys Gly Pro Leu Ser Ser Ile Leu Arg Ala Phe Tyr
            595                 600                 605

<210> SEQ ID NO 20
<211> LENGTH: 495
<212> TYPE: PRT
<213> ORGANISM: Glycine max

<400> SEQUENCE: 20

Met Ala Lys Leu Val Phe Ser Leu Cys Phe Leu Leu Phe Ser Gly Cys
1               5                   10                  15

Cys Phe Ala Phe Ser Ser Arg Glu Gln Pro Gln Gln Asn Glu Cys Gln
            20                  25                  30

Ile Gln Lys Leu Asn Ala Leu Lys Pro Asp Asn Arg Ile Glu Ser Glu
        35                  40                  45

Gly Gly Leu Ile Glu Thr Trp Asn Pro Asn Asn Lys Pro Phe Gln Cys
    50                  55                  60

Ala Gly Val Ala Leu Ser Arg Cys Thr Leu Asn Arg Asn Ala Leu Arg
65                  70                  75                  80

Arg Pro Ser Tyr Thr Asn Gly Pro Gln Glu Ile Tyr Ile Gln Gln Gly
                85                  90                  95

Lys Gly Ile Phe Gly Met Ile Tyr Pro Gly Cys Pro Ser Thr Phe Glu
            100                 105                 110

Glu Pro Gln Gln Pro Gln Gln Arg Gly Gln Ser Ser Arg Pro Gln Asp
        115                 120                 125

Arg His Gln Lys Ile Tyr Asn Phe Arg Glu Gly Asp Leu Ile Ala Val
    130                 135                 140

Pro Thr Gly Val Ala Trp Trp Met Tyr Asn Asn Glu Asp Thr Pro Val
145                 150                 155                 160

Val Ala Val Ser Ile Ile Asp Thr Asn Ser Leu Glu Asn Gln Leu Asp
                165                 170                 175

Gln Met Pro Arg Arg Phe Tyr Leu Ala Gly Asn Gln Glu Gln Glu Phe
            180                 185                 190

Leu Lys Tyr Gln Gln Glu Gln Gly Gly His Gln Ser Gln Lys Gly Lys
        195                 200                 205

His Gln Gln Glu Glu Glu Asn Glu Gly Gly Ser Ile Leu Ser Gly Phe
    210                 215                 220

Thr Leu Glu Phe Leu Glu His Ala Phe Ser Val Asp Lys Gln Ile Ala
225                 230                 235                 240

Lys Asn Leu Gln Gly Glu Asn Glu Gly Glu Asp Lys Gly Ala Ile Val
                245                 250                 255

Thr Val Lys Gly Gly Leu Ser Val Ile Lys Pro Pro Thr Asp Glu Gln
            260                 265                 270

Gln Gln Arg Pro Gln Glu Glu Glu Glu Glu Glu Asp Glu Lys Pro
        275                 280                 285
```

Gln Cys Lys Gly Lys Asp Lys His Cys Gln Arg Pro Arg Gly Ser Gln
            290                 295                 300

Ser Lys Ser Arg Arg Asn Gly Ile Asp Glu Thr Ile Cys Thr Met Arg
305                 310                 315                 320

Leu Arg His Asn Ile Gly Gln Thr Ser Ser Pro Asp Ile Tyr Asn Pro
                325                 330                 335

Gln Ala Gly Ser Val Thr Thr Ala Thr Ser Leu Asp Phe Pro Ala Leu
            340                 345                 350

Ser Trp Leu Arg Leu Ser Ala Glu Phe Gly Ser Leu Arg Lys Asn Ala
        355                 360                 365

Met Phe Val Pro His Tyr Asn Leu Asn Ala Asn Ser Ile Ile Tyr Ala
    370                 375                 380

Leu Asn Gly Arg Ala Leu Ile Gln Val Val Asn Cys Asn Gly Glu Arg
385                 390                 395                 400

Val Phe Asp Gly Glu Leu Gln Glu Gly Arg Val Leu Ile Val Pro Gln
                405                 410                 415

Asn Phe Val Val Ala Ala Arg Ser Gln Ser Asp Asn Phe Glu Tyr Val
            420                 425                 430

Ser Phe Lys Thr Asn Asp Thr Pro Met Ile Gly Thr Leu Ala Gly Ala
        435                 440                 445

Asn Ser Leu Leu Asn Ala Leu Pro Glu Glu Val Ile Gln His Thr Phe
    450                 455                 460

Asn Leu Lys Ser Gln Gln Ala Arg Gln Ile Lys Asn Asn Pro Phe
465                 470                 475                 480

Lys Phe Leu Val Pro Pro Gln Glu Ser Gln Lys Arg Ala Val Ala
                485                 490                 495

<210> SEQ ID NO 21
<211> LENGTH: 485
<212> TYPE: PRT
<213> ORGANISM: Glycine max

<400> SEQUENCE: 21

Met Ala Lys Leu Val Leu Ser Leu Cys Phe Leu Leu Phe Ser Gly Cys
1               5                   10                  15

Phe Ala Leu Arg Glu Gln Ala Gln Asn Glu Cys Gln Ile Gln Lys
            20                  25                  30

Leu Asn Ala Leu Lys Pro Asp Asn Arg Ile Glu Ser Glu Gly Gly Phe
        35                  40                  45

Ile Glu Thr Trp Asn Pro Asn Asn Lys Pro Phe Gln Cys Ala Gly Val
    50                  55                  60

Ala Leu Ser Arg Cys Thr Leu Asn Arg Asn Ala Leu Arg Arg Pro Ser
65                  70                  75                  80

Tyr Thr Asn Gly Pro Gln Glu Ile Tyr Ile Gln Gln Gly Asn Gly Ile
                85                  90                  95

Phe Gly Met Ile Phe Pro Gly Cys Pro Ser Thr Tyr Gln Glu Pro Gln
            100                 105                 110

Glu Ser Gln Gln Arg Gly Arg Ser Gln Arg Pro Gln Asp Arg His Gln
        115                 120                 125

Lys Val His Arg Phe Arg Glu Gly Asp Leu Ile Ala Val Pro Thr Gly
    130                 135                 140

Val Ala Trp Trp Met Tyr Asn Asn Glu Asp Thr Pro Val Val Ala Val
145                 150                 155                 160

Ser Ile Ile Asp Thr Asn Ser Leu Glu Asn Gln Leu Asp Gln Met Pro 165                 170                 175
Arg Arg Phe Tyr Leu Ala Gly Asn Gln Glu Gln Glu Phe Leu Lys Tyr
            180                 185                 190

Gln Gln Gln Gln Gln Gly Gly Ser Gln Ser Gln Lys Gly Lys Gln Gln
        195                 200                 205

Glu Glu Glu Asn Glu Gly Ser Asn Ile Leu Ser Gly Phe Ala Pro Glu
    210                 215                 220

Phe Leu Lys Glu Ala Phe Gly Val Asn Met Gln Ile Val Arg Asn Leu
225                 230                 235                 240

Gln Gly Glu Asn Glu Glu Asp Ser Gly Ala Ile Val Thr Val Lys
            245                 250                 255

Gly Gly Leu Arg Val Thr Ala Pro Ala Met Arg Lys Pro Gln Gln Glu
        260                 265                 270

Glu Asp Asp Asp Glu Glu Gln Pro Gln Cys Val Glu Thr Asp
    275                 280                 285

Lys Gly Cys Gln Arg Gln Ser Lys Arg Ser Arg Asn Gly Ile Asp Glu
        290                 295                 300

Thr Ile Cys Thr Met Arg Leu Arg Gln Asn Ile Gly Gln Asn Ser Ser
305                 310                 315                 320

Pro Asp Ile Tyr Asn Pro Gln Ala Gly Ser Ile Thr Thr Ala Thr Ser
            325                 330                 335

Leu Asp Phe Pro Ala Leu Trp Leu Leu Lys Leu Ser Gln Tyr Gly
        340                 345                 350

Ser Leu Arg Lys Asn Ala Met Phe Val Pro His Tyr Thr Leu Asn Ala
        355                 360                 365

Asn Ser Ile Ile Tyr Ala Leu Asn Gly Arg Ala Leu Val Gln Val Val
370                 375                 380

Asn Cys Asn Gly Glu Arg Val Phe Asp Gly Leu Gln Glu Gly Gly
385                 390                 395                 400

Val Leu Ile Val Pro Gln Asn Phe Ala Val Ala Ala Lys Ser Gln Ser
            405                 410                 415

Asp Asn Phe Glu Tyr Val Ser Phe Lys Thr Asn Asp Arg Pro Ser Ile
        420                 425                 430

Gly Asn Leu Ala Gly Ala Asn Ser Leu Leu Asn Ala Leu Pro Glu Glu
        435                 440                 445

Val Ile Gln His Thr Phe Asn Leu Lys Ser Gln Ala Arg Gln Val
    450                 455                 460

Lys Asn Asn Asn Pro Phe Ser Phe Leu Val Pro Pro Gln Glu Ser Gln
465                 470                 475                 480

Arg Arg Ala Val Ala
            485

<210> SEQ ID NO 22
<211> LENGTH: 481
<212> TYPE: PRT
<213> ORGANISM: Glycine max

<400> SEQUENCE: 22

Met Ala Lys Leu Val Leu Ser Leu Cys Phe Leu Leu Phe Ser Gly Cys
1               5                   10                  15

Cys Phe Ala Phe Ser Phe Arg Glu Gln Pro Gln Gln Asn Glu Cys Gln
            20                  25                  30

Ile Gln Arg Leu Asn Ala Leu Lys Pro Asp Asn Arg Ile Glu Ser Glu
        35                  40                  45

-continued

```
Gly Gly Phe Ile Glu Thr Trp Asn Pro Asn Asn Lys Pro Phe Gln Cys
 50              55                  60

Ala Gly Val Ala Leu Ser Arg Cys Thr Leu Asn Arg Asn Ala Leu Arg
 65                  70                  75                  80

Arg Pro Ser Tyr Thr Asn Ala Pro Gln Glu Ile Tyr Ile Gln Gln Gly
                 85                  90                  95

Ser Gly Ile Phe Gly Met Ile Phe Pro Gly Cys Pro Ser Thr Phe Glu
            100                 105                 110

Glu Pro Gln Gln Lys Gly Gln Ser Arg Pro Gln Asp Arg His Gln
                115                 120                 125

Lys Ile Tyr His Phe Arg Glu Gly Asp Leu Ile Ala Val Pro Thr Gly
130                 135                 140

Phe Ala Tyr Trp Met Tyr Asn Asn Glu Asp Thr Pro Val Val Ala Val
145                 150                 155                 160

Ser Leu Ile Asp Thr Asn Ser Phe Gln Asn Gln Leu Asp Gln Met Pro
                165                 170                 175

Arg Arg Phe Tyr Leu Ala Gly Asn Gln Glu Gln Glu Phe Leu Gln Tyr
            180                 185                 190

Gln Pro Gln Lys Gln Gln Gly Gly Thr Gln Ser Gln Lys Gly Lys Arg
                195                 200                 205

Gln Gln Glu Glu Glu Asn Glu Gly Gly Ser Ile Leu Ser Gly Phe Ala
210                 215                 220

Pro Glu Phe Leu Glu His Ala Phe Val Val Asp Arg Gln Ile Val Arg
225                 230                 235                 240

Lys Leu Gln Gly Glu Asn Glu Glu Glu Lys Gly Ala Ile Val Thr
                245                 250                 255

Val Lys Gly Gly Leu Ser Val Ile Ser Pro Pro Thr Glu Glu Gln Gln
                260                 265                 270

Gln Arg Pro Glu Glu Glu Lys Pro Asp Cys Asp Glu Lys Asp Lys
            275                 280                 285

His Cys Gln Ser Gln Ser Arg Asn Gly Ile Asp Glu Thr Ile Cys Thr
290                 295                 300

Met Arg Leu Arg His Asn Ile Gly Gln Thr Ser Ser Pro Asp Ile Phe
305                 310                 315                 320

Asn Pro Gln Ala Gly Ser Ile Thr Thr Ala Thr Ser Leu Asp Phe Pro
                325                 330                 335

Ala Leu Ser Trp Leu Lys Leu Ser Ala Gln Phe Gly Ser Leu Arg Lys
            340                 345                 350

Asn Ala Met Phe Val Pro His Tyr Asn Leu Asn Ala Asn Ser Ile Ile
                355                 360                 365

Tyr Ala Leu Asn Gly Arg Ala Leu Val Gln Val Val Asn Cys Asn Gly
370                 375                 380

Glu Arg Val Phe Asp Gly Glu Leu Gln Glu Gly Gln Val Leu Ile Val
385                 390                 395                 400

Pro Gln Asn Phe Ala Val Ala Ala Arg Ser Gln Ser Asp Asn Phe Glu
                405                 410                 415

Tyr Val Ser Phe Lys Thr Asn Asp Arg Pro Ser Ile Gly Asn Leu Ala
                420                 425                 430

Gly Ala Asn Ser Leu Leu Asn Ala Leu Pro Glu Glu Val Ile Gln Gln
            435                 440                 445

Thr Phe Asn Leu Arg Arg Gln Gln Ala Arg Gln Val Lys Asn Asn Asn
450                 455                 460

Pro Phe Ser Phe Leu Val Pro Pro Lys Glu Ser Gln Arg Arg Val Val
```

```
                465                 470                 475                 480
Ala

<210> SEQ ID NO 23
<211> LENGTH: 562
<212> TYPE: PRT
<213> ORGANISM: Glycine max

<400> SEQUENCE: 23

Met Gly Lys Pro Phe Thr Leu Ser Leu Ser Ser Leu Cys Leu Leu Leu
1               5                   10                  15

Leu Ser Ser Ala Cys Phe Ala Ile Ser Ser Ser Lys Leu Asn Glu Cys
            20                  25                  30

Gln Leu Asn Asn Leu Asn Ala Leu Glu Pro Asp His Arg Val Glu Ser
        35                  40                  45

Glu Gly Gly Leu Ile Gln Thr Trp Asn Ser Gln His Pro Glu Leu Lys
    50                  55                  60

Cys Ala Gly Val Thr Val Ser Lys Leu Thr Leu Asn Arg Asn Gly Leu
65                  70                  75                  80

His Ser Pro Ser Tyr Ser Pro Tyr Pro Arg Met Ile Ile Ile Ala Gln
                85                  90                  95

Gly Lys Gly Ala Leu Gly Val Ala Ile Pro Gly Cys Pro Glu Thr Phe
            100                 105                 110

Glu Glu Pro Gln Glu Gln Ser Asn Arg Arg Gly Ser Arg Ser Gln Lys
        115                 120                 125

Gln Gln Leu Gln Asp Ser His Gln Lys Ile Arg His Phe Asn Glu Gly
    130                 135                 140

Asp Val Leu Val Ile Pro Pro Ser Val Pro Tyr Trp Thr Tyr Asn Thr
145                 150                 155                 160

Gly Asp Glu Pro Val Val Ala Ile Ser Leu Leu Asp Thr Ser Asn Phe
                165                 170                 175

Asn Asn Gln Leu Asp Gln Thr Pro Arg Val Phe Tyr Leu Ala Gly Asn
            180                 185                 190

Pro Asp Ile Glu Tyr Pro Glu Thr Met Gln Gln Gln Gln Gln Gln Lys
        195                 200                 205

Ser His Gly Gly Arg Lys Gln Gly Gln His Gln Gln Glu Glu Glu Glu
    210                 215                 220

Glu Gly Gly Ser Val Leu Ser Gly Phe Ser Lys His Phe Leu Ala Gln
225                 230                 235                 240

Ser Phe Asn Thr Asn Glu Asp Ile Ala Glu Lys Leu Glu Ser Pro Asp
                245                 250                 255

Asp Glu Arg Lys Gln Ile Val Thr Val Glu Gly Gly Leu Ser Val Ile
            260                 265                 270

Ser Pro Lys Trp Gln Glu Gln Asp Glu Asp Glu Asp Glu Asp Glu
        275                 280                 285

Asp Asp Glu Asp Glu Gln Ile Pro Ser His Pro Arg Arg Pro Ser
    290                 295                 300

His Gly Lys Arg Glu Gln Asp Glu Asp Glu Asp Glu Asp Lys
305                 310                 315                 320

Pro Arg Pro Ser Arg Pro Ser Gln Gly Lys Arg Asn Lys Thr Gly Gln
                325                 330                 335

Asp Glu Asp Glu Asp Glu Asp Glu Asp Gln Pro Arg Lys Ser Arg Glu
            340                 345                 350

Trp Arg Ser Lys Lys Thr Gln Pro Arg Arg Pro Arg Gln Glu Glu Pro
```

```
                355                 360                 365
Arg Glu Arg Gly Cys Glu Thr Arg Asn Gly Val Glu Glu Asn Ile Cys
370                 375                 380

Thr Leu Lys Leu His Glu Asn Ile Ala Arg Pro Ser Arg Ala Asp Phe
385                 390                 395                 400

Tyr Asn Pro Lys Ala Gly Arg Ile Ser Thr Leu Asn Ser Leu Thr Leu
                405                 410                 415

Pro Ala Leu Arg Gln Phe Gln Leu Ser Ala Gln Tyr Val Val Leu Tyr
                420                 425                 430

Lys Asn Gly Ile Tyr Ser Pro His Trp Asn Leu Asn Ala Asn Ser Val
                435                 440                 445

Ile Tyr Val Thr Arg Gly Gln Gly Lys Val Arg Val Val Asn Cys Gln
                450                 455                 460

Gly Asn Ala Val Phe Asp Gly Glu Leu Arg Arg Gly Gln Leu Leu Val
465                 470                 475                 480

Val Pro Gln Asn Phe Val Val Ala Glu Gln Ala Gly Glu Gln Gly Phe
                485                 490                 495

Glu Tyr Ile Val Phe Lys Thr His His Asn Ala Val Thr Ser Tyr Leu
                500                 505                 510

Lys Asp Val Phe Arg Ala Ile Pro Ser Glu Val Leu Ala His Ser Tyr
                515                 520                 525

Asn Leu Arg Gln Ser Gln Val Ser Glu Leu Lys Tyr Glu Gly Asn Trp
                530                 535                 540

Gly Pro Leu Val Asn Pro Glu Ser Gln Gln Gly Ser Pro Arg Val Lys
545                 550                 555                 560

Val Ala

<210> SEQ ID NO 24
<211> LENGTH: 562
<212> TYPE: PRT
<213> ORGANISM: Glycine max

<400> SEQUENCE: 24

Met Gly Lys Pro Phe Thr Leu Ser Leu Ser Ser Leu Cys Leu Leu Leu
1               5                   10                  15

Leu Ser Ser Ala Cys Phe Ala Ile Ser Ser Lys Leu Asn Glu Cys
                20                  25                  30

Gln Leu Asn Asn Leu Asn Ala Leu Glu Pro Asp His Arg Val Glu Phe
            35                  40                  45

Glu Gly Gly Leu Ile Gln Thr Trp Asn Ser Gln His Pro Glu Leu Lys
    50                  55                  60

Cys Ala Gly Val Thr Val Ser Lys Leu Thr Leu Asn Arg Asn Gly Leu
65                  70                  75                  80

His Leu Pro Ser Tyr Ser Pro Tyr Pro Arg Met Ile Ile Ile Ala Gln
                85                  90                  95

Gly Lys Gly Ala Leu Gln Cys Lys Pro Gly Cys Pro Glu Thr Phe Glu
            100                 105                 110

Glu Pro Gln Glu Gln Ser Asn Arg Arg Gly Ser Arg Ser Gln Lys Gln
        115                 120                 125

Gln Leu Gln Asp Ser His Gln Lys Ile Arg His Phe Asn Glu Gly Asp
    130                 135                 140

Val Leu Val Ile Pro Pro Gly Val Pro Tyr Trp Thr Tyr Asn Thr Gly
145                 150                 155                 160

Asp Glu Pro Val Val Ala Ile Ser Leu Leu Asp Thr Ser Asn Phe Asn
```

```
                    165                 170                 175
Asn Gln Leu Asp Gln Thr Pro Arg Val Phe Tyr Leu Ala Gly Asn Pro
                180                 185                 190

Asp Ile Glu Tyr Pro Glu Thr Met Gln Gln Gln Gln Gln Lys Ser
            195                 200                 205

His Gly Gly Arg Lys Gln Gly Gln His Gln Gln Glu Glu Glu
        210                 215                 220

Gly Gly Ser Val Leu Ser Gly Phe Ser Lys His Phe Leu Ala Gln Ser
225                 230                 235                 240

Phe Asn Thr Asn Glu Asp Ile Ala Glu Lys Leu Gln Ser Pro Asp Asp
                245                 250                 255

Glu Arg Lys Gln Ile Val Thr Val Glu Gly Gly Leu Ser Val Ile Ser
            260                 265                 270

Pro Lys Trp Gln Glu Gln Gln Asp Glu Asp Glu Asp Glu Asp
        275                 280                 285

Asp Glu Asp Glu Gln Ile Pro Ser His Pro Arg Arg Pro Ser His
    290                 295                 300

Gly Lys Arg Glu Gln Asp Glu Asp Glu Asp Glu Asp Lys Pro
305                 310                 315                 320

Arg Pro Ser Arg Pro Ser Gln Gly Lys Arg Glu Gln Asp Gln Asp Gln
                325                 330                 335

Asp Glu Asp Glu Asp Glu Asp Gln Pro Arg Lys Ser Arg Glu
            340                 345                 350

Trp Arg Ser Lys Lys Thr Gln Pro Arg Arg Pro Arg Gln Glu Glu Pro
                355                 360                 365

Arg Glu Arg Gly Cys Glu Thr Arg Asn Gly Val Glu Glu Asn Ile Cys
            370                 375                 380

Thr Leu Lys Leu His Glu Asn Ile Ala Arg Pro Ser Arg Ala Asp Phe
385                 390                 395                 400

Tyr Asn Pro Lys Ala Gly Arg Ile Ser Thr Leu Asn Ser Leu Thr Leu
                405                 410                 415

Pro Ala Leu Arg Gln Phe Gln Leu Ser Ala Gln Tyr Val Val Leu Tyr
                420                 425                 430

Lys Asn Gly Ile Tyr Ser Pro His Trp Asn Leu Asn Ala Asn Ser Val
            435                 440                 445

Ile Tyr Val Thr Arg Gly Gln Gly Lys Val Arg Val Asn Cys Gln
        450                 455                 460

Gly Asn Ala Val Phe Asp Gly Glu Leu Arg Arg Gly Gln Leu Leu Val
465                 470                 475                 480

Val Pro Gln Asn Phe Val Val Ala Glu Gln Ala Gly Glu Gln Gly Phe
                485                 490                 495

Glu Tyr Ile Val Phe Lys Thr His His Asn Ala Val Thr Ser Tyr Leu
            500                 505                 510

Lys Asp Val Phe Arg Ala Ile Pro Ser Glu Val Leu Ala His Ser Tyr
            515                 520                 525

Asn Leu Arg Gln Ser Gln Val Ser Glu Leu Lys Tyr Glu Gly Asn Trp
        530                 535                 540

Gly Pro Leu Val Asn Pro Glu Ser Gln Gln Gly Ser Pro Arg Val Lys
545                 550                 555                 560

Val Ala

<210> SEQ ID NO 25
<211> LENGTH: 203
```

```
<212> TYPE: PRT
<213> ORGANISM: Glycine max

<400> SEQUENCE: 25

Met Lys Ser Thr Ile Phe Phe Ala Leu Phe Val Cys Ala Phe Thr
1               5                   10                  15

Ile Ser Tyr Leu Pro Ser Ala Thr Ala Gln Phe Val Leu Asp Thr Asp
                20                  25                  30

Asp Asp Pro Leu Gln Asn Gly Gly Thr Tyr Tyr Met Leu Pro Val Met
            35                  40                  45

Arg Gly Lys Gly Gly Gly Ile Glu Val Asp Ser Thr Gly Lys Glu Ile
        50                  55                  60

Cys Pro Leu Thr Val Val Gln Ser Pro Asn Glu Leu Asp Lys Gly Ile
65                  70                  75                  80

Gly Leu Val Phe Thr Ser Pro Leu His Ala Leu Phe Ile Ala Glu Arg
                85                  90                  95

Tyr Pro Leu Ser Ile Lys Phe Gly Ser Phe Ala Val Ile Thr Leu Cys
            100                 105                 110

Ala Gly Met Pro Thr Glu Trp Ala Ile Val Glu Arg Glu Gly Leu Gln
        115                 120                 125

Ala Val Lys Leu Ala Ala Arg Asp Thr Val Asp Gly Trp Phe Asn Ile
    130                 135                 140

Glu Arg Val Ser Arg Glu Tyr Asn Asp Tyr Lys Leu Val Phe Cys Pro
145                 150                 155                 160

Gln Gln Ala Glu Asp Asn Lys Cys Glu Asp Ile Gly Ile Gln Ile Asp
                165                 170                 175

Asp Asp Gly Ile Arg Arg Leu Val Leu Ser Lys Asn Lys Pro Leu Val
            180                 185                 190

Val Gln Phe Gln Lys Phe Arg Ser Ser Thr Ala
        195                 200

<210> SEQ ID NO 26
<211> LENGTH: 216
<212> TYPE: PRT
<213> ORGANISM: Glycine max

<400> SEQUENCE: 26

Met Lys Ser Thr Ile Phe Phe Leu Phe Leu Phe Cys Ala Phe Thr Thr
1               5                   10                  15

Ser Tyr Leu Pro Ser Ala Ile Ala Asp Phe Val Leu Asp Asn Glu Gly
            20                  25                  30

Asn Pro Leu Glu Asn Gly Gly Thr Tyr Tyr Ile Leu Ser Asp Ile Thr
        35                  40                  45

Ala Phe Gly Gly Ile Arg Ala Ala Pro Thr Gly Asn Glu Arg Cys Pro
    50                  55                  60

Leu Thr Val Val Gln Ser Arg Asn Glu Leu Asp Lys Gly Ile Gly Thr
65                  70                  75                  80

Ile Ile Ser Ser Pro Tyr Arg Ile Arg Phe Ile Ala Glu Gly His Pro
                85                  90                  95

Leu Ser Leu Lys Phe Asp Ser Phe Ala Val Ile Met Leu Cys Val Gly
            100                 105                 110

Ile Pro Thr Glu Trp Ser Val Val Glu Asp Leu Pro Glu Gly Pro Ala
        115                 120                 125

Val Lys Ile Gly Glu Asn Lys Asp Ala Met Asp Gly Trp Phe Arg Leu
    130                 135                 140
```

Glu Arg Val Ser Asp Asp Glu Phe Asn Asn Tyr Lys Leu Val Phe Cys
145                 150                 155                 160

Pro Gln Gln Ala Glu Asp Asp Lys Cys Gly Asp Ile Gly Ile Ser Ile
            165                 170                 175

Asp His Asp Asp Gly Thr Arg Arg Leu Val Val Ser Lys Asn Lys Pro
            180                 185                 190

Leu Val Val Gln Phe Gln Lys Leu Asp Lys Glu Ser Leu Ala Lys Lys
            195                 200                 205

Asn His Gly Leu Ser Arg Ser Glu
        210                 215

<210> SEQ ID NO 27
<211> LENGTH: 476
<212> TYPE: PRT
<213> ORGANISM: Glycine max

<400> SEQUENCE: 27

Met Gly Asn Lys Thr Thr Leu Leu Leu Leu Phe Val Leu Cys His
1               5                   10                  15

Gly Val Ala Thr Thr Thr Met Ala Phe His Asp Asp Glu Gly Gly Asp
            20                  25                  30

Lys Lys Ser Pro Lys Ser Leu Phe Leu Met Ser Asn Ser Thr Arg Val
            35                  40                  45

Phe Lys Thr Asp Ala Gly Glu Met Arg Val Leu Lys Ser His Gly Gly
50                  55                  60

Arg Ile Phe Tyr Arg His Met His Ile Gly Phe Ile Ser Met Glu Pro
65                  70                  75                  80

Lys Ser Leu Phe Val Pro Gln Tyr Leu Asp Ser Asn Leu Ile Ile Phe
                85                  90                  95

Ile Arg Arg Gly Glu Ala Lys Leu Gly Phe Ile Tyr Asp Asp Glu Leu
            100                 105                 110

Ala Glu Arg Arg Leu Lys Thr Gly Asp Leu Tyr Met Ile Pro Ser Gly
            115                 120                 125

Ser Ala Phe Tyr Leu Val Asn Ile Gly Glu Gly Gln Arg Leu His Val
130                 135                 140

Ile Cys Ser Ile Asp Pro Ser Thr Ser Leu Gly Leu Glu Thr Phe Gln
145                 150                 155                 160

Ser Phe Tyr Ile Gly Gly Gly Ala Asn Ser His Ser Val Leu Ser Gly
                165                 170                 175

Phe Glu Pro Ala Ile Leu Glu Thr Ala Phe Asn Glu Ser Arg Thr Val
            180                 185                 190

Val Glu Glu Ile Phe Ser Lys Glu Leu Asp Gly Pro Ile Met Phe Val
            195                 200                 205

Asp Asp Ser His Ala Pro Ser Leu Trp Thr Lys Phe Leu Gln Leu Lys
210                 215                 220

Lys Asp Asp Lys Glu Gln Gln Leu Lys Lys Met Met Gln Asp Gln Glu
225                 230                 235                 240

Glu Asp Glu Glu Glu Lys Gln Thr Ser Arg Ser Trp Arg Lys Leu Leu
            245                 250                 255

Glu Thr Val Phe Gly Lys Val Asn Glu Lys Ile Glu Asn Lys Asp Thr
            260                 265                 270

Ala Gly Ser Pro Ala Ser Tyr Asn Leu Tyr Asp Lys Lys Ala Asp
            275                 280                 285

Phe Lys Asn Ala Tyr Gly Trp Ser Lys Ala Leu His Gly Gly Glu Tyr
            290                 295                 300

Pro Pro Leu Ser Glu Pro Asp Ile Gly Val Leu Leu Val Lys Leu Ser
305                 310                 315                 320

Ala Gly Ser Met Leu Ala Pro His Val Asn Pro Ile Ser Asp Glu Tyr
            325                 330                 335

Thr Ile Val Leu Ser Gly Tyr Gly Glu Leu His Ile Gly Tyr Pro Asn
            340                 345                 350

Gly Ser Arg Ala Met Lys Thr Lys Ile Lys Gln Gly Asp Val Phe Val
            355                 360                 365

Val Pro Arg Tyr Phe Pro Phe Cys Gln Val Ala Ser Arg Asp Gly Pro
370                 375                 380

Leu Glu Phe Phe Gly Phe Ser Thr Ser Ala Arg Lys Asn Lys Pro Gln
385                 390                 395                 400

Phe Leu Ala Gly Ala Ala Ser Leu Leu Arg Thr Leu Met Gly Pro Glu
            405                 410                 415

Leu Ser Ala Ala Phe Gly Val Ser Glu Asp Thr Leu Arg Arg Ala Val
            420                 425                 430

Asp Ala Gln His Glu Ala Val Ile Leu Pro Ser Ala Trp Ala Ala Pro
            435                 440                 445

Pro Glu Asn Ala Gly Lys Leu Lys Met Glu Glu Pro Asn Ala Ile
    450                 455                 460

Arg Ser Phe Ala Asn Asp Val Val Met Asp Val Phe
465                 470                 475

<210> SEQ ID NO 28
<211> LENGTH: 379
<212> TYPE: PRT
<213> ORGANISM: Glycine max

<400> SEQUENCE: 28

Met Gly Phe Leu Val Leu Leu Leu Phe Ser Leu Leu Gly Leu Ser Ser
1               5                   10                  15

Ser Ser Ser Ile Ser Thr His Arg Ser Ile Leu Asp Leu Asp Leu Thr
            20                  25                  30

Lys Phe Thr Thr Gln Lys Gln Val Ser Ser Leu Phe Gln Leu Trp Lys
        35                  40                  45

Ser Glu His Gly Arg Val Tyr His Asn His Glu Glu Glu Ala Lys Arg
50                  55                  60

Leu Glu Ile Phe Lys Asn Asn Leu Asn Tyr Ile Arg Asp Met Asn Ala
65                  70                  75                  80

Asn Arg Lys Ser Pro His Ser His Arg Leu Gly Leu Asn Lys Phe Ala
                85                  90                  95

Asp Ile Thr Pro Gln Glu Phe Ser Lys Lys Tyr Leu Gln Ala Pro Lys
            100                 105                 110

Asp Val Ser Gln Gln Ile Lys Met Ala Asn Lys Lys Met Lys Lys Glu
            115                 120                 125

Gln Tyr Ser Cys Asp His Pro Pro Ala Ser Trp Asp Trp Arg Lys Lys
        130                 135                 140

Gly Val Ile Thr Gln Val Lys Tyr Gln Gly Gly Cys Gly Ser Gly Trp
145                 150                 155                 160

Ala Phe Ser Ala Thr Gly Ala Ile Glu Ala Ala His Ala Ile Ala Thr
                165                 170                 175

Gly Asp Leu Val Ser Leu Ser Glu Gln Glu Leu Val Asp Cys Val Glu
            180                 185                 190

Glu Ser Glu Gly Cys Tyr Asn Gly Trp His Tyr Gln Ser Phe Glu Trp

```
            195                 200                 205
Val Leu Glu His Gly Ile Ala Thr Asp Asp Tyr Pro Tyr Arg
210                 215                 220

Ala Lys Glu Gly Arg Cys Lys Ala Asn Lys Ile Gln Asp Lys Val Thr
225                 230                 235                 240

Ile Asp Gly Tyr Glu Thr Leu Ile Met Ser Asp Glu Ser Thr Glu Ser
                245                 250                 255

Glu Thr Glu Gln Ala Phe Leu Ser Ala Ile Leu Glu Gln Pro Ile Ser
            260                 265                 270

Val Ser Ile Asp Ala Lys Asp Phe His Leu Tyr Thr Gly Gly Ile Tyr
        275                 280                 285

Asp Gly Glu Asn Cys Thr Ser Pro Tyr Gly Ile Asn His Phe Val Leu
    290                 295                 300

Leu Val Gly Tyr Gly Ser Ala Asp Gly Val Asp Tyr Trp Ile Ala Lys
305                 310                 315                 320

Asn Ser Trp Gly Glu Asp Trp Gly Glu Asp Gly Tyr Ile Trp Ile Gln
                325                 330                 335

Arg Asn Thr Gly Asn Leu Leu Gly Val Cys Gly Met Asn Tyr Phe Ala
            340                 345                 350

Ser Tyr Pro Thr Lys Glu Glu Ser Glu Thr Leu Val Ser Ala Arg Val
        355                 360                 365

Lys Gly His Arg Arg Val Asp His Ser Pro Leu
    370                 375

<210> SEQ ID NO 29
<211> LENGTH: 158
<212> TYPE: PRT
<213> ORGANISM: Glycine max

<400> SEQUENCE: 29

Met Thr Lys Phe Thr Ile Leu Leu Ile Ser Leu Leu Phe Cys Ile Ala
1               5                   10                  15

His Thr Cys Ser Ala Ser Lys Trp Gln His Gln Asp Ser Cys Arg
            20                  25                  30

Lys Gln Leu Gln Gly Val Asn Leu Thr Pro Cys Glu Lys His Ile Met
        35                  40                  45

Glu Lys Ile Gln Gly Arg Gly Asp Asp Asp Asp Asp Asp Asp Asp
    50                  55                  60

Asn His Ile Leu Arg Thr Met Arg Gly Arg Ile Asn Tyr Ile Arg Arg
65                  70                  75                  80

Asn Glu Gly Lys Asp Glu Asp Glu Glu Glu Gly His Met Gln Lys
                85                  90                  95

Cys Cys Thr Glu Met Ser Glu Leu Arg Ser Pro Lys Cys Gln Cys Lys
            100                 105                 110

Ala Leu Gln Lys Ile Met Glu Asn Gln Ser Glu Glu Leu Glu Glu Lys
        115                 120                 125

Gln Lys Lys Lys Met Glu Lys Glu Leu Ile Asn Leu Ala Thr Met Cys
    130                 135                 140

Arg Phe Gly Pro Met Ile Gln Cys Asp Leu Ser Ser Asp Asp
145                 150                 155

<210> SEQ ID NO 30
<211> LENGTH: 280
<212> TYPE: PRT
<213> ORGANISM: Glycine max
```

<400> SEQUENCE: 30

Met Ala Thr Ser Asn Phe Ser Ile Val Leu Ser Leu Ser Leu Ala Phe
1               5                   10                  15

Phe Leu Val Leu Leu Thr Lys Ala Asn Ser Thr Asn Thr Val Ser Phe
            20                  25                  30

Thr Val Ser Lys Phe Ser Pro Arg Gln Gln Asn Leu Ile Phe Gln Gly
        35                  40                  45

Asp Ala Ala Ile Ser Pro Ser Gly Val Leu Arg Leu Thr Lys Val Asp
    50                  55                  60

Ser Ile Asp Val Pro Thr Thr Gly Ser Leu Gly Arg Ala Leu Tyr Ala
65                  70                  75                  80

Thr Pro Ile Gln Ile Trp Asp Ser Glu Thr Gly Lys Val Ala Ser Trp
                85                  90                  95

Ala Thr Ser Phe Lys Phe Lys Val Phe Ser Pro Asn Lys Thr Ala Asp
            100                 105                 110

Gly Leu Ala Phe Phe Leu Ala Pro Val Gly Ser Lys Pro Gln Ser Lys
        115                 120                 125

Gly Gly Phe Leu Gly Leu Phe Asn Ser Asp Ser Lys Asn Lys Ser Val
130                 135                 140

Gln Thr Val Ala Val Glu Phe Asp Thr Tyr Tyr Asn Ala Lys Trp Asp
145                 150                 155                 160

Pro Ala Asn Arg His Ile Gly Ile Asp Val Asn Ser Ile Lys Ser Val
                165                 170                 175

Lys Thr Ala Ser Trp Gly Leu Ala Asn Gly Gln Ile Ala Gln Ile Leu
            180                 185                 190

Ile Thr Tyr Asp Ala Asp Thr Ser Leu Leu Val Ala Ser Leu Ile His
        195                 200                 205

Pro Ser Arg Lys Thr Ser Tyr Ile Leu Ser Glu Thr Val Ser Leu Lys
    210                 215                 220

Ser Asn Leu Pro Glu Trp Val Asn Ile Gly Phe Ser Ala Thr Thr Gly
225                 230                 235                 240

Leu Asn Lys Gly Phe Val Glu Thr His Asp Val Phe Ser Trp Ser Phe
                245                 250                 255

Ala Ser Lys Leu Ser Asp Gly Ser Thr Ser Asp Thr Leu Asp Leu Pro
            260                 265                 270

Ser Phe Leu Leu Asn Glu Ala Ile
        275                 280

<210> SEQ ID NO 31
<211> LENGTH: 864
<212> TYPE: PRT
<213> ORGANISM: Glycine max

<400> SEQUENCE: 31

Met Phe Gly Ile Phe Asp Lys Gly Gln Lys Ile Lys Gly Thr Val Val
1               5                   10                  15

Leu Met Pro Lys Asn Val Leu Asp Phe Asn Ala Ile Thr Ser Ile Gly
            20                  25                  30

Lys Gly Gly Val Ile Asp Thr Ala Thr Gly Ile Leu Gly Gln Gly Val
        35                  40                  45

Ser Leu Val Gly Gly Val Ile Asp Thr Ala Thr Ser Phe Leu Gly Arg
    50                  55                  60

Asn Ile Ser Met Gln Leu Ile Ser Ala Thr Gln Thr Asp Gly Ser Gly
65                  70                  75                  80

```
Asn Gly Lys Val Gly Lys Glu Val Tyr Leu Glu Lys His Leu Pro Thr
             85                  90                  95

Leu Pro Thr Leu Gly Ala Arg Gln Asp Ala Phe Ser Ile Phe Phe Glu
        100                 105                 110

Trp Asp Ala Ser Phe Gly Ile Pro Gly Ala Phe Tyr Ile Lys Asn Phe
            115                 120                 125

Met Thr Asp Glu Phe Phe Leu Val Ser Val Lys Leu Glu Asp Ile Pro
    130                 135                 140

Asn His Gly Thr Ile Glu Phe Val Cys Asn Ser Trp Val Tyr Asn Phe
145                 150                 155                 160

Arg Ser Tyr Lys Lys Asn Arg Ile Phe Phe Val Asn Asp Thr Tyr Leu
                165                 170                 175

Pro Ser Ala Thr Pro Ala Pro Leu Leu Lys Tyr Arg Lys Glu Glu Leu
            180                 185                 190

Glu Val Leu Arg Gly Asp Gly Thr Gly Lys Arg Lys Asp Phe Asp Arg
        195                 200                 205

Ile Tyr Asp Tyr Asp Val Tyr Asn Asp Leu Gly Asn Pro Asp Gly Gly
    210                 215                 220

Asp Pro Arg Pro Ile Leu Gly Gly Ser Ser Ile Tyr Pro Tyr Pro Arg
225                 230                 235                 240

Arg Val Arg Thr Gly Arg Glu Arg Thr Arg Thr Asp Pro Asn Ser Glu
                245                 250                 255

Lys Pro Gly Glu Val Tyr Val Pro Arg Asp Glu Asn Phe Gly His Leu
            260                 265                 270

Lys Ser Ser Asp Phe Leu Thr Tyr Gly Ile Lys Ser Leu Ser His Asp
        275                 280                 285

Val Ile Pro Leu Phe Lys Ser Ala Ile Phe Gln Leu Arg Val Thr Ser
    290                 295                 300

Ser Glu Phe Glu Ser Phe Glu Asp Val Arg Ser Leu Tyr Glu Gly Gly
305                 310                 315                 320

Ile Lys Leu Pro Thr Asp Ile Leu Ser Gln Ile Ser Pro Leu Pro Ala
                325                 330                 335

Leu Lys Glu Ile Phe Arg Thr Asp Gly Glu Asn Val Leu Gln Phe Pro
            340                 345                 350

Pro Pro His Val Ala Lys Val Ser Lys Ser Gly Trp Met Thr Asp Glu
        355                 360                 365

Glu Phe Ala Arg Glu Val Ile Ala Gly Val Asn Pro Asn Val Ile Arg
    370                 375                 380

Arg Leu Gln Glu Phe Pro Pro Lys Ser Thr Leu Asp Pro Thr Leu Tyr
385                 390                 395                 400

Gly Asp Gln Thr Ser Thr Ile Thr Lys Glu Gln Leu Glu Ile Asn Met
                405                 410                 415

Gly Gly Val Thr Val Glu Glu Ala Leu Ser Thr Gln Arg Leu Phe Ile
            420                 425                 430

Leu Asp Tyr Gln Asp Ala Phe Ile Pro Tyr Leu Thr Arg Ile Asn Ser
        435                 440                 445

Leu Pro Thr Ala Lys Ala Tyr Ala Thr Arg Thr Ile Leu Phe Leu Lys
    450                 455                 460

Asp Asp Gly Thr Leu Lys Pro Leu Ala Ile Glu Leu Ser Lys Pro His
465                 470                 475                 480

Pro Asp Gly Asp Asn Leu Gly Pro Glu Ser Ile Val Val Leu Pro Ala
                485                 490                 495

Thr Glu Gly Val Asp Ser Thr Ile Trp Leu Leu Ala Lys Ala His Val
```

```
                500             505             510
Ile Val Asn Asp Ser Gly Tyr His Gln Leu Val Ser His Trp Leu Asn
            515             520             525

Thr His Ala Val Met Glu Pro Phe Ala Ile Ala Thr Asn Arg His Leu
        530             535             540

Ser Val Leu His Pro Ile Tyr Lys Leu Leu Tyr Pro His Tyr Arg Asp
545             550             555             560

Thr Ile Asn Ile Asn Gly Leu Ala Arg Gln Ser Leu Ile Asn Ala Asp
            565             570             575

Gly Ile Ile Glu Lys Ser Phe Leu Pro Gly Lys Tyr Ser Ile Glu Met
        580             585             590

Ser Ser Ser Val Tyr Lys Asn Trp Val Phe Thr Asp Gln Ala Leu Pro
    595             600             605

Ala Asp Leu Val Lys Arg Gly Leu Ala Ile Glu Asp Pro Ser Ala Pro
610             615             620

His Gly Leu Arg Leu Val Ile Glu Asp Tyr Pro Tyr Ala Val Asp Gly
625             630             635             640

Leu Glu Ile Trp Asp Ala Ile Lys Thr Trp Val His Glu Tyr Val Ser
            645             650             655

Leu Tyr Tyr Pro Thr Asp Ala Ala Val Gln Gln Asp Thr Glu Leu Gln
        660             665             670

Ala Trp Trp Lys Glu Ala Val Glu Lys Gly His Gly Asp Leu Lys Glu
    675             680             685

Lys Pro Trp Trp Pro Lys Met Gln Thr Thr Glu Asp Leu Ile Gln Ser
690             695             700

Cys Ser Ile Ile Val Trp Thr Ala Ser Ala Leu His Ala Ala Val Asn
705             710             715             720

Phe Gly Gln Tyr Pro Tyr Gly Gly Leu Ile Leu Asn Arg Pro Thr Leu
            725             730             735

Ala Arg Arg Phe Ile Pro Ala Glu Gly Thr Pro Glu Tyr Asp Glu Met
        740             745             750

Val Lys Asn Pro Gln Lys Ala Tyr Leu Arg Thr Ile Thr Pro Lys Phe
    755             760             765

Glu Thr Leu Ile Asp Leu Ser Val Ile Glu Ile Leu Ser Arg His Ala
770             775             780

Ser Asp Glu Ile Tyr Leu Gly Glu Arg Glu Thr Pro Asn Trp Thr Thr
785             790             795             800

Asp Lys Lys Ala Leu Glu Ala Phe Lys Arg Phe Gly Ser Lys Leu Thr
            805             810             815

Gly Ile Glu Gly Lys Ile Asn Ala Arg Asn Ser Asp Pro Ser Leu Arg
        820             825             830

Asn Arg Thr Gly Pro Val Gln Leu Pro Tyr Thr Leu Leu His Arg Ser
    835             840             845

Ser Glu Glu Gly Leu Thr Phe Lys Gly Ile Pro Asn Ser Ile Ser Ile
850             855             860

<210> SEQ ID NO 32
<211> LENGTH: 13
<212> TYPE: PRT
<213> ORGANISM: Glycine max

<400> SEQUENCE: 32

Ala Ala Glu Leu Ala Ser Met Ser Ala Gly Ala Val Lys
1               5                   10
```

<210> SEQ ID NO 33
<211> LENGTH: 8
<212> TYPE: PRT
<213> ORGANISM: Glycine max

<400> SEQUENCE: 33

Ala Met Gly Asp Ile Gly Gly Arg
1               5

<210> SEQ ID NO 34
<211> LENGTH: 15
<212> TYPE: PRT
<213> ORGANISM: Glycine max

<400> SEQUENCE: 34

Asp Thr Pro Gln Gly Ser Ile Glu Ala Leu Gln Ala Gly Glu Arg
1               5                   10                  15

<210> SEQ ID NO 35
<211> LENGTH: 9
<212> TYPE: PRT
<213> ORGANISM: Glycine max

<400> SEQUENCE: 35

Asp Tyr Thr Leu Gln Ala Ala Glu Lys
1               5

<210> SEQ ID NO 36
<211> LENGTH: 11
<212> TYPE: PRT
<213> ORGANISM: Glycine max

<400> SEQUENCE: 36

Gly Leu Ala Ala Ser Ala Gly Glu Thr Ala Lys
1               5                   10

<210> SEQ ID NO 37
<211> LENGTH: 7
<212> TYPE: PRT
<213> ORGANISM: Glycine max

<400> SEQUENCE: 37

Gln Ser Trp Leu Glu Thr Arg
1               5

<210> SEQ ID NO 38
<211> LENGTH: 8
<212> TYPE: PRT
<213> ORGANISM: Glycine max

<400> SEQUENCE: 38

Ser Ala Ala Gly Tyr Ala Ala Lys
1               5

<210> SEQ ID NO 39
<211> LENGTH: 13
<212> TYPE: PRT
<213> ORGANISM: Glycine max

<400> SEQUENCE: 39

Ser Ala Gly Gly Thr Thr Ala Ser Tyr Val Gly Glu Lys
1               5                   10

<210> SEQ ID NO 40

```
<211> LENGTH: 18
<212> TYPE: PRT
<213> ORGANISM: Glycine max

<400> SEQUENCE: 40

Ser Ala Trp Glu Gln Ile Ser Asn Tyr Ser Asp Gln Ala Thr Gln Gly
1               5                   10                  15

Val Lys

<210> SEQ ID NO 41
<211> LENGTH: 8
<212> TYPE: PRT
<213> ORGANISM: Glycine max

<400> SEQUENCE: 41

Ser Leu Thr Ser Ile Gly Glu Lys
1               5

<210> SEQ ID NO 42
<211> LENGTH: 11
<212> TYPE: PRT
<213> ORGANISM: Glycine max

<400> SEQUENCE: 42

Thr Thr Ala Val Ile Thr Cys Thr Leu Glu Lys
1               5                   10

<210> SEQ ID NO 43
<211> LENGTH: 6
<212> TYPE: PRT
<213> ORGANISM: Glycine max

<400> SEQUENCE: 43

Val Ala Ala Asp Leu Arg
1               5
```

METHODS AND SYSTEMS FOR SELECTIVE QUANTITATION AND DETECTION OF ALLERGENS INCLUDING GLY M 7

CROSS REFERENCE TO RELATED APPLICATION

This is a national phase entry under 35 U.S.C. § 371 of international patent application PCT/US2018/14765, filed on Jan. 23, 2018 and published in English as international patent publication WO2018140370 on Aug. 2, 2018, which claims priority to the benefit of U.S. Provisional Patent Application Ser. No. 62/450,246 filed Jan. 25, 2017 the disclosure of which is hereby incorporated by reference in its entirety.

BACKGROUND OF THE INVENTION

The current methods for analysis of gene expression in plants that are preferred in the art include DNA-based techniques (for example PCR and/or RT-PCR); the use of reporter genes; Southern blotting; and immunochemistry. All of these methodologies suffer from various shortcomings. Detection of known and potential allergens in plants, plant parts, and/or food products is an important subject for public safety.

Although mass spectrometry has been disclosed previously, existing approaches are limited without selected and sensitive quantitation. There remains a need for a high-throughput method for selected and sensitive quantitation of known and/or potential allergens in plant, plant parts, and/or food products.

SUMMARY OF THE INVENTION

The invention relates to methods and systems taking advantage of bioinformatic investigations to identify candidate signature peptides for quantitative multiplex analysis of complex protein samples from plants, plant parts, and/or food products using mass spectrometry. Provided are use and methods for selecting candidate signature peptides for quantitation using a bioinformatic approach. Also provided are systems comprising a chromatography and mass spectrometry for using selected signature peptides.

In one aspect, provided is a method of selecting candidate signature peptide for quantitation of known allergen and potential allergens from a plant-based sample. The method comprises:
(a) identifying potential allergens based on homology to at least one known allergen protein sequence;
(b) performing sequence alignment of the at least one known allergen and potential allergens identified in step (a);
(c) selecting a consensus sequence or representative sequence based on the sequence alignment;
(d) determining a plural of candidate signature peptides based on conservative regions or domains from the sequence alignment and in silico digestion data of the consensus sequence or representative sequence selected in Step (c); and
(e) quantitating the amount of the at least one known allergen and potential allergens in the plant-based sample based on measurements of the signature peptides.

In one embodiment, the quantitating step uses a column chromatography and mass spectrometry. In another embodiment, the quantitating step comprises measuring the plural of candidate signature peptides using high resolution accurate mass spectrometry (HRAM MS). In another embodiment, the quantitating step comprises calculating corresponding peak heights or peak areas of the candidate signature peptides from mass spectrometry. In another embodiment, the quantitating step comprises comparing data from high fragmentation mode and low fragmentation mode from mass spectrometry.

In one embodiment, the at least one known allergen comprises Gly m 7. In another embodiment, the at least one known allergen comprises at least one allergen selected from the group consisting of Gly m 1, Gly m 3, Gly m 4, Gly m 5 (beta-conglycinin), Gly m 6 (Glycinin) G1, Gly m 6 (Glycinin) G2, Gly m 6 (Glycinin) G3, Gly m 6 (Glycinin) G4, Gly m 6 (Glycinin) precursor, Gly m 6 (Glycinin) G4 precursor, Gly m 7, Kunitz trypsin inhibitor 1, Kunitz trypsin inhibitor 3, Gly m Bd 28 K, Gly m Bd 30 K, Gly m 8 (2S albumin), Lectin, and lipoxygenase. In another embodiment, the potential allergens comprise at least one sequence selected from SEQ ID NOs: 12-15. In another embodiment, the candidate signature peptides comprise at least one sequence selected from SEQ ID NOs: 32-43. In another embodiment, the candidate signature peptides comprise SEQ ID NO: 32, 33, 37, or 41. In another embodiment, the plant-based sample comprises a soybean seed or part of a soybean seed.

In another aspect, provided is a system for quantitating one or more protein of interest with known amino acid sequence in a plant-based sample. The system comprises:
(a) a high-throughput means for extracting proteins from a plant-based sample;
(b) a process module for digesting extracted proteins with at least one protease;
(c) a separation module for separating peptides in a single step;
(d) a selection module for selecting a plural of signature peptides for at least one known allergen and potential allergens; and
(e) a mass spectrometry for measuring the plural of signature peptides.

In one embodiment, the separation module comprises a column chromatography. In a further embodiment, the column chromatography comprises a liquid column chromatography. In another embodiment, the mass spectrometry comprises a high resolution accurate mass spectrometry (HRAM MS). In another embodiment, the selection module uses a method provided herein.

In one embodiment, the at least one known allergen comprises Gly m 7. In another embodiment, the at least one known allergen comprises at least one allergen selected from the group consisting of Gly m 1, Gly m 3, Gly m 4, Gly m 5 (beta-conglycinin), Gly m 6 (Glycinin) G1, Gly m 6 (Glycinin) G2, Gly m 6 (Glycinin) G3, Gly m 6 (Glycinin) G4, Gly m 6 (Glycinin) precursor, Gly m 6 (Glycinin) G4 precursor, Gly m 7, Kunitz trypsin inhibitor 1, Kunitz trypsin inhibitor 3, Gly m Bd 28 K, Gly m Bd 30 K, Gly m 8 (2S albumin), Lectin, and lipoxygenase. In another embodiment, the potential allergens comprise at least one sequence selected from SEQ ID NOs: 12-15. In another embodiment, the signature peptides comprise at least one sequence selected from SEQ ID NOs: 32-43. In another embodiment, the signature peptides comprise SEQ ID NO: 32, 33, 37, or 41. In another embodiment, the plant-based sample comprises a soybean seed or part of a soybean seed.

In another aspect, provided is a high-throughput method of quantitating at least one allergen with known amino acid sequence and homologous potential allergens in a plant-based sample. The method comprises using the system provided herein.

BRIEF DESCRIPTION OF THE FIGURES

FIG. 14 shows sequences alignments among potential homologs of Gly m 7.

DETAILED DESCRIPTION OF THE INVENTION

Figure 1:
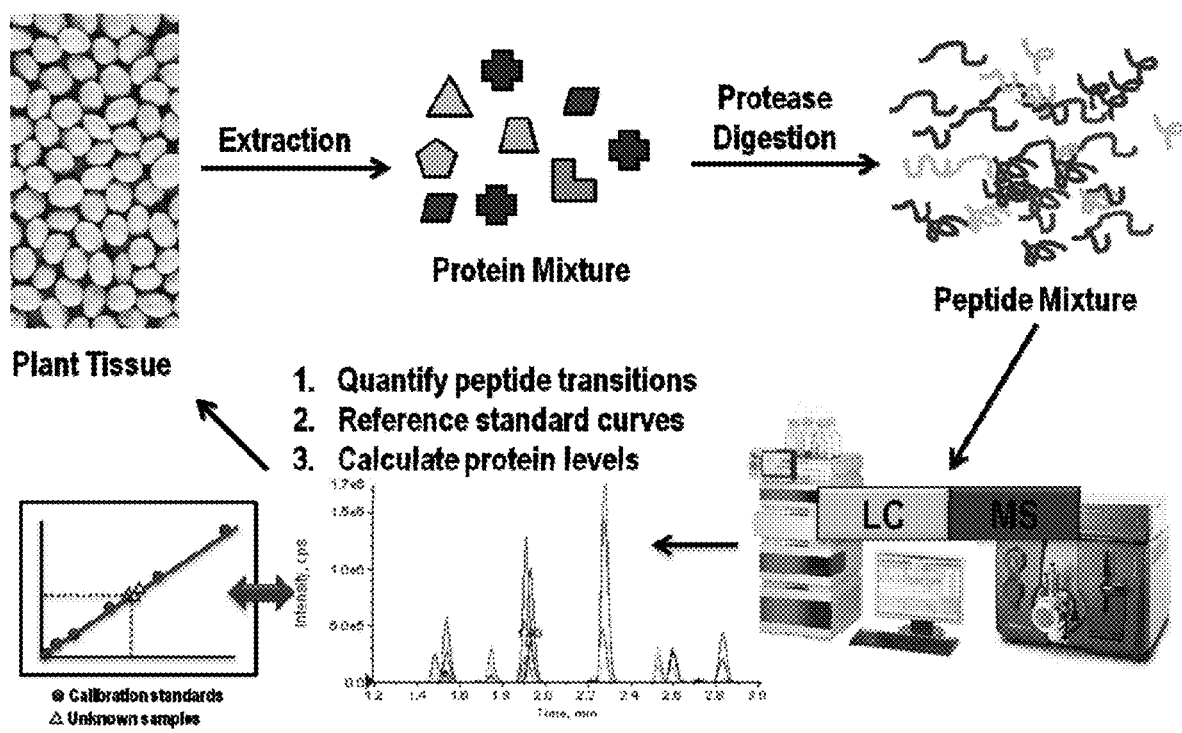
FIG. 1 shows a representative analysis work flow for the methods and systems disclosed herein.

It is of significance to enable a sensitive multiplex assay that is capable of selectively detecting and measuring levels of proteins of interest. Currently, relevant technologies for protein expression detection rely heavily on traditional immunochemistry technologies which present a challenge to accommodate the volume of data required to generate per sample.

Soybean is a multi-billion dollar commodity due to its balanced composition of 2:2:1 protein, starch, and oil by weight. Many seeds, including soybeans, contain proteins that are allergens and anti-nutritional factors. As such, there are concerns regarding the potential of altering allergen levels in genetically-modified soybean varieties when compared to varieties developed through traditional breeding. The measurement of allergen levels in crops has been achieved almost exclusively by immunoassays, such as enzyme-linked immunosorbent assays (ELISA) or IgE-immunoblotting; however, these methods suffer from limited sensitivity and specificity and high variability.

There has been recent interest in developing LC-MS/MS based methods to quantify several plant-expressed proteins in a single analysis. Analysis using these "signature peptides" involves tracking protein expression levels by quantifying several highly specific digest fragments of the proteins of interest. This can be typically accomplished using liquid chromatography coupled with selected reaction monitoring (SRM) tandem mass spectrometry. Improved multiplexed LC-MS/MS methods and systems are provided herein to enable simultaneous quantitation(s) of several allergen proteins in transgenic and non-transgenic soybean. Methods and systems provided herein are validated for analytical figures of merit including accuracy, precision, linearity, limits of detection and quantitation; and for other considerations including sample throughput, transferability, and ease of use. The allergens can be quantified using a multiplexing format and samples can be harvested from the field, processed, and analyzed/quantitated for example within a day (twenty-four hours) window (from field to measured numerical value). In addition, sample preparations of the methods and systems provided can be fully scalable for high-throughput, thus enabling hundreds of samples to be analyzed in a single batch.

Representative soybean allergens include, for example, Gly m 1, Gly m 3, Gly m 4, Gly m 5 (beta-conglycinin), Gly m 6 (Glycinin) G1, Gly m 6 (Glycinin) G2, Gly m 6 (Glycinin) G3, Gly m 6 (Glycinin) G4, Gly m 6 (Glycinin) precursor, Gly m 6 (Glycinin) G4 precursor, Kunitz trypsin inhibitor 1, Kunitz trypsin inhibitor 3, Gly m Bd 28 K, Gly m Bd 30 K, Gly m 8 (2S albumin), Lectin, and lipoxygenase.

Representative wheat allergens include, for example, profilin (Tri a12), wheat lipid transfer protein 1 (Tri a14), agglutinin isolectin 1 (Tri a18), omega-5 gliadin—seed storage protein (Tri a19), gliadin (Tri a20; NCBI Accession Nos. M10092, M11073, M11074, M11075, M11076, K03074, and K03075), thioredoxin (Tri a25), high molecular weight glutenin (Tri a26), low molecular weight glutenin (Tri a36), and alpha purothionin (Tri a37).

Representative corn allergens include, for example, maize lipid transfer protein (LTP) (*Zea* m14) and thioredoxin (*Zea* m25).

Representative corn allergens include, for example, rice profilin A (Ory s12).

In some embodiments, the methods and systems provided use liquid chromatography coupled to tandem mass spectrometry (LC-MS/MS) to detect protein expression levels of sixteen different allergens from soybean. In some embodiments, the methods and systems enable analysis of each allergen by itself or combined with additional proteins for a multiplexing assay for qualitative and quantitative analysis in plant matrices.

In some embodiments, the mass spectrometry detection for quantitative studies may be accomplished using selected reaction monitoring, performed on a triple quadrupole mass spectrometer. Using this type of instrumentation, initial mass-selection of ion (peptide) of interest formed in the source, followed by, dissociation of this precursor ion in the collision region of the MS, then mass-selection, and counting, of a specific product (daughter) ion. In some embodiments, the mass spectrometry detection for quantitative studies may be accomplished using selected reaction monitoring (SRM). Using particular type of instrumentation, initial mass-selection of ion of interest formed in the source, followed by, dissociation of this precursor (protein) ion in the collision region of the mass spectrometer (MS), then mass-selection, and counting, of a specific product (peptide) ion. In some embodiment, counts per unit time may provide an integratable peak area from which amounts or concentration of analytes can be determined. In some embodiment, the use of high resolution accurate mass (HRAM) monitoring for quantitation, performed on a HRAM capable mass spectrometer, may include, but is not limited to, hybrid quadrupole-time-of-flight, quadrupole-orbitrap, ion trap-orbitrap, or quadrupole-ion-trap-orbitrap (tribrid) mass spectrometers. Using particular type of instrumentation, peptides are not subject to fragmentation conditions, but rather are measured as intact peptides using full scan or targeted scan modes (for example selective ion monitoring mode or SIM). Integratable peak area can be determined by generating an extracted ion chromatogram for each specific analyte and amounts or concentration of analytes can be calculated. The high resolution and accurate mass nature of the data enable highly specific and sensitive ion signals for the analyte (protein and/or peptide) of interest.

Unless otherwise stated, the following terms used in this application, including the specification and claims, have the definitions given below. It must be noted that, as used in the specification and the appended claims, the singular forms "a," "an," and "the" include plural referents unless the context clearly dictates otherwise.

As used herein, the term "bioconfinement" refers to restriction of the movement of genetically modified plants or their genetic material to designated areas. The term includes physical, physicochemical, biological confinement, as well as other forms of confinement that prevent the survival, spread or reproduction of a genetically modified plants in the natural environment or in artificial growth conditions.

As used herein, the term "complex protein sample" is used to distinguish a sample from a purified protein sample. A complex protein sample contains multiple proteins, and may additionally contain other contaminants.

As used herein, the general term "mass spectrometry" or "MS" refers to any suitable mass spectrometry method, device or configuration including, e.g., electrospray ionization (ESI), matrix-assisted laser desorption/ionization (MALDI) MS, MALDI-time of flight (TOF) MS, atmospheric pressure (AP) MALDI MS, vacuum MALDI MS, or combinations thereof. Mass spectrometry devices measure the molecular mass of a molecule (as a function of the molecule's mass-to-charge ratio) by measuring the molecule's flight path through a set of magnetic and electric fields. The mass-to-charge ratio is a physical quantity that is widely used in the electrodynamics of charged particles. The mass-to-charge ratio of a particular peptide can be calculated, a priori, by one of skill in the art. Two particles with different mass-to-charge ratio will not move in the same path in a vacuum when subjected to the same electric and magnetic fields.

Mass spectrometry instruments consist of three modules: an ion source, which splits the sample molecules into ions; a mass analyzer, which sorts the ions by their masses by applying electromagnetic fields; and a detector, which measures the value of an indicator quantity and thus provides data for calculating the abundances of each ion present. The technique has both qualitative and quantitative applications. These include identifying unknown compounds, determining the isotopic composition of elements in a molecule, determining the structure of a compound by observing its fragmentation, and quantifying the amount of a compound in a sample.

A detailed overview of mass spectrometry methodologies and devices can be found in the following references which are hereby incorporated by reference: Can and Annan (1997) Overview of peptide and protein analysis by mass spectrometry. In: *Current Protocols in Molecular Biology*, edited by Ausubel, et al. New York: Wiley, p. 10.21.1-10.21.27; Paterson and Aebersold (1995) *Electrophoresis* 16: 1791-1814; Patterson (1998) Protein identification and characterization by mass spectrometry. In: *Current Protocols in Molecular Biology*, edited by Ausubel, et al. New York: Wiley, p. 10.22.1-10.22.24; and Domon and Aebersold (2006) *Science* 312(5771):212-17.

As the term is used herein, proteins and/or peptides are "multiplexed" when two or more proteins and/or peptides of interest are present in the same sample.

As used herein, a "plant trait" may refer to any single feature or quantifiable measurement of a plant.

As used herein, the phrase "peptide" or peptides" may refer to short polymers formed from the linking, in a defined order, of α-amino acids. Peptides may also be generated by the digestion of polypeptides, for example proteins, with a protease.

As used herein, the phrase "protein" or proteins" may refer to organic compounds made of amino acids arranged in a linear chain and joined together by peptide bonds between the carboxyl and amino groups of adjacent amino acid residues. The sequence of amino acids in a protein is defined by the sequence of a gene, which is encoded in the genetic code. In general, the genetic code specifies 20 standard amino acids, however in certain organisms the genetic code can include selenocysteine—and in certain archaea-pyrrolysine. The residues in a protein are often observed to be chemically modified by post-translational modification, which can happen either before the protein is used in the cell, or as part of control mechanisms. Protein residues may also be modified by design, according to techniques familiar to those of skill in the art. As used herein, the term "protein" encompasses linear chains comprising naturally occurring amino acids, synthetic amino acids, modified amino acids, or combinations of any or all of the above.

As used herein, the term "single injection" refers to the initial step in the operation of a MS or LC-MS device. When a protein sample is introduced into the device in a single injection, the entire sample is introduced in a single step.

As used herein, the phrase "signature peptide" refers an identifier (short peptide) sequence of a specific protein. Any protein may contain an average of between 10 and 100 signature peptides. Typically signature peptides have at least one of the following criteria: easily detected by mass spectroscopy, predictably and stably eluted from a liquid chromatography (LC) column, enriched by reversed phase high performance liquid chromatography (RP-HPLC), good ionization, good fragmentation, or combinations thereof. A peptide that is readily quantified by mass spectrometry typically has at least one of the following criteria: readily synthesized, ability to be highly purified (>97%), soluble in ≤20% acetonitrile, low non-specific binding, oxidation resistant, post-synthesis modification resistant, and a hydrophobicity or hydrophobicity index ≥10 and ≤40. The hydrophobicity index can be calculated according to Krokhin, Molecular and Cellular Proteomics 3 (2004) 908, which is incorporated by reference. It's known that a peptide having a hydrophobicity index less than 10 or greater than 40 may not be reproducibly resolved or eluted by a RP-HPLC column.

As used herein, the term "stacked" refers to the presence of multiple heterologous polynucleotides incorporated in the genome of a plant.

Tandem mass spectrometry: In tandem mass spectrometry, a parent ion generated from a molecule of interest may be filtered in a mass spectrometry instrument, and the parent ion subsequently fragmented to yield one or more daughter ions that are then analyzed (detected and/or quantified) in a second mass spectrometry procedure. In some embodiments, the use of tandem mass spectrometry is excluded. In these embodiments, tandem mass spectrometry is not used in the methods and systems provided. Thus, neither parent ions nor daughter ions are generated in these embodiments.

As used herein, the term "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenic plants initially so altered as well as those created by sexual crosses or asexual propagation from the initial transgenic plant.

Any plants that provide useful plant parts may be treated in the practice of the present invention. Examples include plants that provide flowers, fruits, vegetables, and grains.

As used herein, the phrase "plant" includes dicotyledonous plants and monocotyledonous plants. Examples of dicotyledonous plants include tobacco, *Arabidopsis*, soybean, tomato, *papaya*, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledonous plants include corn, rice, wheat, sugarcane, barley, rye, sorghum, orchids, bamboo, banana, cattails, lilies, oat, onion, millet, and triticale. Examples of fruit include banana, pineapple, oranges, grapes, grapefruit, watermelon, melon, apples, peaches, pears, kiwifruit, mango, nectarines, guava, persimmon, avocado, lemon, fig, and berries. Examples of flowers include baby's breath, carnation, dahlia, daffodil, geranium, *gerbera*, lily, orchid, peony, Queen Anne's lace, rose, snapdragon, or other cut-flowers or ornamental flowers, potted-flowers, and flower bulbs.

The specificity allowed in a mass spectrometry approach for identifying a single protein from a complex sample is unique in that only the sequence of the protein of interest is required in order to identify the protein of interest. Compared to other formats of multiplexing, mass spectrometry is unique in being able to exploit the full length of a protein's primary amino acid sequence to target unique identifier-type portions of a protein's primary amino acid sequence to virtually eliminate non-specific detection. In some embodiments of the present invention, a proteolytic fragment or set of proteolytic fragments that uniquely identifies a protein(s) of interest is used to detect the protein(s) of interest in a complex protein sample.

In some embodiments, disclosed methods enable the quantification or determination of ratios of multiple proteins in a complex protein sample by a single mass spectrometry analysis, as opposed to measuring each protein of interest individually multiple times and compiling the individual results into one sample result.

In some embodiments, the present disclosure also provides methods useful for the development and use of transgenic plant technology. Specifically, disclosed methods may be used to maintain the genotype of transgenic plants through successive generations. Also, some embodiments of the methods disclosed herein may be used to provide high-throughput analysis of non-transgenic plants that are at risk of being contaminated with transgenes from neighboring plants, for example, by cross-pollination. By these embodiments, bioconfinement of transgenes may be facilitated and/or accomplished. In other embodiments, methods disclosed herein may be used to screen the results of a plant transformation procedure in a high-throughput manner to identify transformants that exhibit desirable expression characteristics The mass-to-charge ratio may be determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as a "mass filter" and "mass detector" for the ions injected into the instrument.

Collision-induced dissociation ("CID") is often used to generate the daughter ions for further detection. In CID, parent ions gain energy through collisions with an inert gas, such as argon, and subsequently fragmented by a process referred to as "unimolecular decomposition." Sufficient energy must be deposited in the parent ion so that certain bonds within the ion can be broken due to increased energy.

The mass spectrometer typically provides the user with an ion scan; that is, the relative abundance of each m/z over a given range (for example 10 to 1200 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards (e.g., internal standards and external standards) can be run with the samples and a standard curve constructed based on ions generated from those standards. Using such a standard curve, the relative abundance of a given ion can be converted into an absolute amount of the original molecule. Numerous other methods for relating the presence or amount of an ion to the presence or amount of the original molecule are well known to those of ordinary skill in the art.

The choice of ionization method can be determined based on the analyte to be measured, type of sample, the type of detector, the choice of positive versus negative mode, etc. Ions can be produced using a variety of methods including, but not limited to, electron ionization, chemical ionization, fast atom bombardment, field desorption, and matrix-assisted laser desorption ionization (MALDI), surface enhanced laser desorption ionization (SELDI), desorption electrospray ionization (DESI), photon ionization, electrospray ionization, and inductively coupled plasma. Electrospray ionization refers to methods in which a solution is passed along a short length of capillary tube, to the end of which is applied a high positive or negative electric potential. Solution reaching the end of the tube, is vaporized (nebulized) into a jet or spray of very small droplets of solution in solvent vapor. This mist of droplets flows through an evaporation chamber which is heated to prevent condensation and to evaporate solvent. As the droplets get smaller the electrical surface charge density increases until such time that the natural repulsion between like charges causes ions as well as neutral molecules to be released.

The effluent of an LC may be injected directly and automatically (i.e., "in-line") into the electrospray device. In some embodiments, proteins contained in an LC effluent are first ionized by electrospray into a parent ion.

Various different mass analyzers can be used in liquid chromatography-mass spectrometry combination (LC-MS). Exemplary mass analyzers include, but not limited to, single quadrupole, triple quadrupole, ion trap, TOF (time of flight), and quadrupole-time of flight (Q-TOF).

The quadrupole mass analyzer may consist of 4 circular rods, set parallel to each other. In a quadrupole mass spectrometer (QMS), the quadrupole is the component of the instrument responsible for filtering sample ions, based on their mass-to-charge ratio (m/z). Ions are separated in a quadrupole based on the stability of their trajectories in the oscillating electric fields that are applied to the rods.

An ion trap is a combination of electric or magnetic fields that captures ions in a region of a vacuum system or tube. Ion traps can be used in mass spectrometry while the ion's quantum state is manipulated.

Time-of-flight mass spectrometry (TOFMS) is a method of mass spectrometry in which an ion's mass-to-charge ratio is determined via a time measurement. Ions are accelerated by an electric field of known strength. This acceleration results in an ion having the same kinetic energy as any other ion that has the same charge. The velocity of the ion depends on the mass-to-charge ratio. The time that it subsequently takes for the particle to reach a detector at a known distance is measured. This time will depend on the mass-to-charge ratio of the particle (heavier particles reach lower speeds). From this time and the known experimental parameters one can find the mass-to-charge ratio of the ion.

In some embodiments, the particular instrument used by the methods and/or systems provided may comprise a high fragmentation mode and a low fragmentation mode (or alternatively a non-fragmentation mode). Such different modes may include alternating scan high and low energy acquisition methodology to generate high resolution mass data. In some embodiments, the high resolution mass data may comprise a product data set (for example data derived from product ion (fragmented ions) under the high fragmentation mode) and a precursor data set (for example data derived from precursor ions (unfragmented ions) under the low fragmentation or non-fragmentation mode).

In some embodiments, the methods and/or systems provided use a mass spectrometer comprising a filtering device that may be used in the selection step, a fragmentation device that may be used in the fragmentation step, and/or one or more mass analyzers that may be used in the acquisition and/or mass spectrum creation step or steps.

The filtering device and/or mass analyzer may comprise a quadrupole. The selection step and/or acquisition step and/or mass spectrum creation step or steps may involve the use of a resolving quadrupole. Additionally or alternatively, the filtering device may comprise a two dimensional or three dimensional ion trap or time-of-flight (ToF) mass analyzer. The mass analyzer or mass analyzers may comprise or further comprise one or more of a time-of-flight mass analyzer and/or an ion cyclotron resonance mass analyzer and/or an orbitrap mass analyzer and/or a two dimensional or three dimensional ion trap.

Filtering by means of selection based upon mass-to-charge ratio (m/z) can be achieved by using a mass analyzer which can select ions based upon m/z, for example a quadrupole; or to transmit a wide m/z range, separate ions according to their m/z, and then select the ions of interest by means of their m/z value. An example of the latter would be a time-of-flight mass analyzer combined with a timed ion selector(s). The methods and/or systems provided may comprise isolating and/or separating the one or more proteins of interest, for example from two or more of a plurality of proteins, using a chromatographic technique for example liquid chromatography (LC). The method may further comprise measuring an elution time for the protein of interest and/or comparing the measured elution time with an expected elution time.

Additionally or alternatively, the proteins of interest may be separated using an ion mobility technique, which may be carried out using an ion mobility cell. Additionally, the proteins of interest may be selected by order or time of ion mobility drift. The method may further comprise measuring a drift time for the proteins of interest and/or comparing the measured drift time with an expected drift time.

In some embodiments, the methods and/or systems provided are label-free, where quantitation can be achieved by comparison of the peak intensity, or area under the mass spectral peak for the precursor or product m/z values of interest between injections and across samples. In some embodiments, internal standard normalization may be used to account for any known associated analytical error. Another label-free method of quantification, spectral counting, involves summing the number of fragment ion spectra, or scans, that are acquired for each given peptide, in a non-redundant or redundant fashion. The associated peptide mass spectra for each protein are then summed, providing a measure of the number of scans per protein with this being proportional to its abundance. Comparison can then be made between samples/injections.

In some embodiments, the ion source is selected from the group consisting of: (1) an electrospray ionization ("ESI") ion source; (2) an atmospheric pressure photo ionization ("APPI") ion source; (3) an atmospheric pressure chemical ionization ("APCI") ion source; (4) a matrix assisted laser desorption ionization ("MALDI") ion source; (5) a laser desorption ionization ("LDI") ion source; (6) an atmospheric pressure ionization ("API") ion source; (7) a desorption ionization on silicon ("DIOS") ion source; (8) an electron impact ("EI") ion source; (9) a chemical ionization ("CI") ion source; (10) a field ionization ("FI") ion source; (11) a field desorption ("FD") ion source; (12) an inductively coupled plasma ("ICP") ion source; (13) a fast atom bombardment ("FAB") ion source; (14) a liquid secondary ion mass spectrometry ("LSIMS") ion source; (15) a desorption electrospray ionization ("DESI") ion source; (16) a nickel-63 radioactive ion source; (17) an atmospheric pressure matrix assisted laser desorption ionization ion source; and (18) a thermospray ion source.

In some embodiments, the methods and/or systems provided comprise an apparatus and/or control system configured to execute a computer program element comprising computer readable program code means for causing a processor to execute a procedure to implement the methods.

In some embodiments, the methods and/or systems provided use an alternating low and elevated energy scan function in combination with liquid chromatography separation of a plant extract. A list of information for proteins of interest can be provided including, but is not limited to, m/z of precursor ion, m/z of product ions, retention time, ion mobility drift time and rate of change of mobility. During the course of the LC separation and as the target ions elute into the mass spectrometer (and as either low energy precursor ions, or elevated energy product ions are detected, or the retention time window is activated) the mass analyzer of the methods and/or systems provided may select a narrow m/z range (of a variable and changeable width) to pass ions through to the gas cell. Accordingly, the signal to noise ratio can be enhanced significantly for quantification of proteins of interest.

In some embodiments, at a chromatographic retention time when a targeted protein of interest is about to elute into the mass spectrometer ion source, the mass analyzer of the methods and/or systems provided can select a narrow m/z range (of a variable and changeable width) according to the targeted precursor ion. These selected ions are then transferred to an instrument stage capable of dissociating the ions by means of alternate and repeated switches between a high fragmentation mode where the sample precursor ions are substantially fragmented into product ions and a low fragmentation mode (or non-fragmentation mode) where the sample precursor ions are not substantially fragmented. Typically high resolution, accurate mass spectra are acquired in both modes and at the end of the experiment associated precursor and product ions are recognized by the closeness in fit of their chromatographic elution times and optionally other physicochemical properties. The signal intensity of either the precursor ion or the product ion associated with targeted proteins of interest can be used to determine the quantity of the proteins in the plant extract.

Those skilled in the art would understand certain variation can exist based on the disclosure provided. Thus, the following examples are given for the purpose of illustrating the invention and shall not be construed as being a limitation on the scope of the invention or claims.

EXAMPLES

Example 1

The methods and systems provided are used for determination of endogenous soybean allergen proteins in soybean seed including Gly m 1, Gly m 3, Gly m 4, Gly m 5 (beta-conglycinin), Gly m 6, Kunitz trypsin inhibitor 1, Kunitz trypsin inhibitor 3, Gly m Bd 28 K, Gly m Bd 30 K, and Gly m 8 (2S albumin). A 100±0.5 mg ground soybean seed sample is defatted twice with hexanes and dried before extracting with extraction buffer containing 5 M urea, 2 M thiourea, 50 mM Tris pH 8.0 and 65 mM DTT. The sample is sonicated in a water bath for thirty minutes, vortexed for one minute, sonicated for another thirty minutes and centrifuged at >3,000 rpm for ten minutes at 4° C.

TABLE 1

Preparation of signature peptide calibration standards

| Initial concentration (ng/mL) | Standard | Volume of Dilution Cocktail (µL) | Volume of Std. (µL) | Final concentration (ng/mL) |
|---|---|---|---|---|
| 5880.00 | Std 12 | — | — | 500.00 |
| 500.00 | Std 11 | 200 | 200 | 250.00 |
| 250.00 | Std 10 | 200 | 200 | 125.00 |
| 125.00 | Std 9 | 200 | 200 | 62.50 |
| 62.50 | Std 8 | 200 | 200 | 31.25 |
| 31.25 | Std 7 | 200 | 200 | 15.63 |
| 15.63 | Std 6 | 200 | 200 | 7.81 |
| 7.81 | Std 5 | 200 | 200 | 3.91 |
| 3.91 | Std 4 | 200 | 200 | 1.95 |
| 1.95 | Std 3 | 200 | 200 | 0.98 |
| 0.98 | Std 2 | 200 | 200 | 0.49 |
| 0.49 | Std 1 | 2000 | 2000 | 0.24 |

The aqueous supernatant is collected and diluted to bring the endogenous soybean allergen protein concentration into the calibration standard range with extraction buffer. The diluted extract is denatured at 95° C. for twenty minutes with the additional 1 M Tris pH 8.0, 0.5 M DTT and deionized water followed by refrigeration at 4° C. for ten minutes. The denatured extract is incubated overnight (~15 hours) at 37° C. with 0.5 mg/mL trypsin enzyme. The digestion reaction is quenched with formic acid water (50/50 v/v) and centrifuge at >3,000 rpm for ten minutes at 4° C. An aliquot of digested extract is transferred to an autosampler vial and analyzed along with calibration standard by liquid chromatography with positive-ion electrospray (ESI) tandem mass spectrometry (LC-MS/MS). Calibration standards of signature peptides are prepared as listed in Table 1.

The limits of detection (LOD) and limits of quantitation (LOQ) for endogenous soybean allergens in this example are set forth in Table 2, where LOD and LOQ represent protein concentration (ng/mg).

TABLE 2

Limits of detection (LOD) and limits of quantitation (LOQ) for endogenous soybean allergens in Example 1 (LOD and LOQ represent protein concentration)

| Allergen | Signature peptide | LOD (ng/mg) | LOQ (ng/mg) |
|---|---|---|---|
| Gly m 1 | SYPSNATCPR (SEQ ID NO: 1) | 0.23 | 0.46 |
| Gly m 3 | YMVIQGEPGAVIR (SEQ ID NO: 2) | 0.20 | 0.39 |
| Gly m 5 | NILEASYDTK (SEQ ID NO: 3) | 1.22 | 2.44 |
| Glycinin G2 | VTAPAMR (SEQ ID NO: 4) | 1.46 | 2.92 |
| Glycinin G3 | NNNPFSFLVPPK (SEQ ID NO: 5) | 1.58 | 3.16 |
| Glycinin precursor | NGLHLPSYSPYPR (SEQ ID NO: 6) | 3.41 | 6.81 |
| Kunitz trypsin inhibitor 1 | GGGIEVDSTGK (SEQ ID NO: 7) | — | — |
| Kunitz trypsin inhibitor 3 | GIGTLLSSPYR (SEQ ID NO: 8) | — | — |
| Gly m Bd 28 K | NKPQFLAGAASLLR (SEQ ID NO: 9) | 5.70 | 11.40 |
| Gly m Bd 30 K | GVITQVK (SEQ ID NO: 10) | 1.15 | 2.30 |
| Gly m 8 | IMENQSEELEEK (SEQ ID NO: 11) | 0.25 | 0.50 |

Concentrations of allergens are calculated from quantitation of signature peptides (for example Analyst Bioanalytical software for LC-MS/MS), and validated by other methods including enzyme-linked immunosorbent assays (ELISA). Calculated concentrations of allergens from different samples are compared using statistical analysis, and results show good consistency among samples.

Example 2

Several homologous protein sequences for Gly m 7 are identified from public databases including NCBI, Phytozome, and UniProt. Identified sequences (SEQ ID NOs: 12-15) are analyzed using bioinformatics tools to identify sequence homology and shared sequence composition among the available protein sequences (see FIG. 14). Specifically this involved the use of Vector NTI Align X alignment tool which performs a CLUSTAL W type alignment. From this analysis, a consensus sequence and/or representative sequence can be determined.

Once the consensus sequence and/or representative sequence is chosen or determined, it is digested in silico to generate candidate signature peptide fragments to be detected and measured by LC-MS. According to the unique approaches provided herein, signature peptides are selected based on the degree of conservation among the available protein sequences, such that the selected signature peptide can be used to quantify all or as many protein isoforms as possible among the identified protein sequences found in the public sequence databases. As a result, quantitation of selected signature peptides can not only measure Gly m 7 itself, but also measure potential allergens which are highly homologous to Gly m 7.

Soybean seed samples are ground to a fine powder, defatted twice with hexane, and extracted with suitable assay buffer (for example 5 M urea, 2 M thiourea, 50 mM Tris (pH 8.0), 65 mM DTT). The samples are sonicated in buffer to extract proteins. The extracted proteins are diluted, denatured, and then proteolytically digested by adding trypsin protease and incubating at 37° C. for 15-20 hours. The digestion reactions are acidified with formic acid (pH=1-2) and are analyzed using LC-MS/MS.

Figure 2:
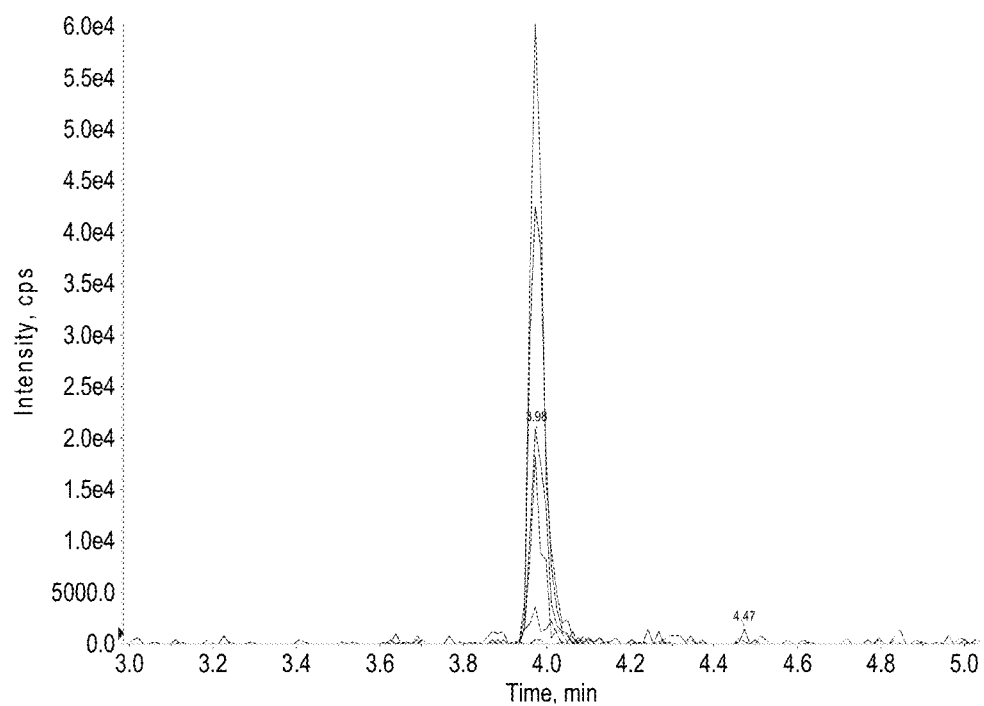
FIGS. 2-13 show representative SRM LC-MS/MS for selected signature peptides SEQ ID NO: 32 AAELASMSAGAVK; SEQ ID NO: 33 AMGDIGGR; SEQ ID NO: 34 DTPQGSIEALQAGER, SEQ ID NO: 35 DYTLQAAEK, SEQ ID NO: 36 GLAASAGETAK, SEQ ID NO: 37 QSWLETR, SEQ ID NO: 38 SAAGYAAK, SEQ ID NO: 39 SAGGTTASYVGEK, SEQ ID NO: 40 SAWEQISNYSDQATQGVK, SEQ ID NO: 41 SLTSIGEK, SEQ ID NO: 42 TTAVITCTLEK, and SEQ ID NO: 43 VAADLR from soybean sample chromatogram.
Figure 3:
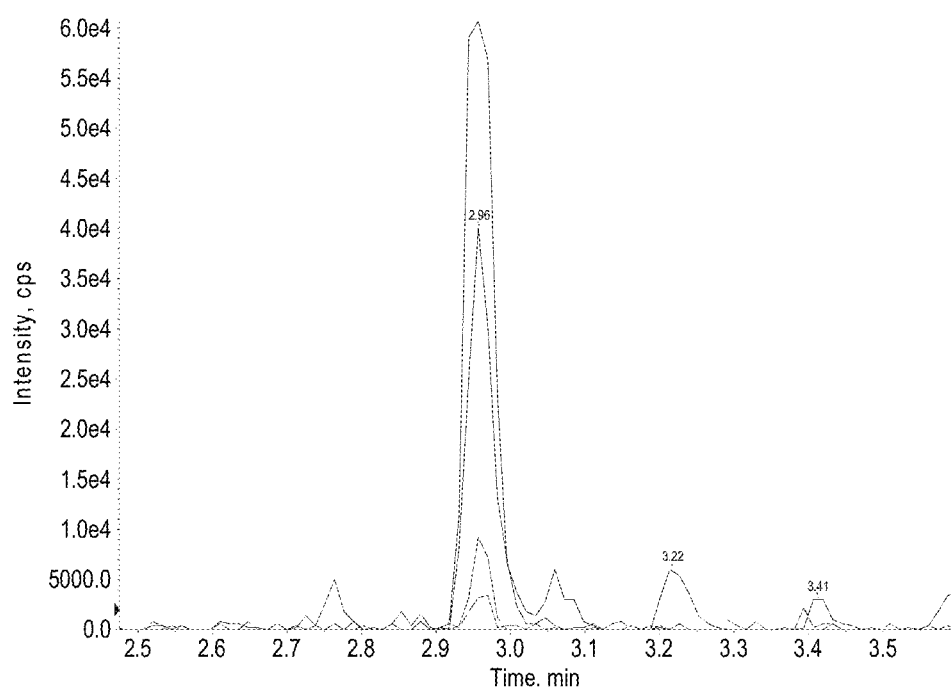
Figure 4A:
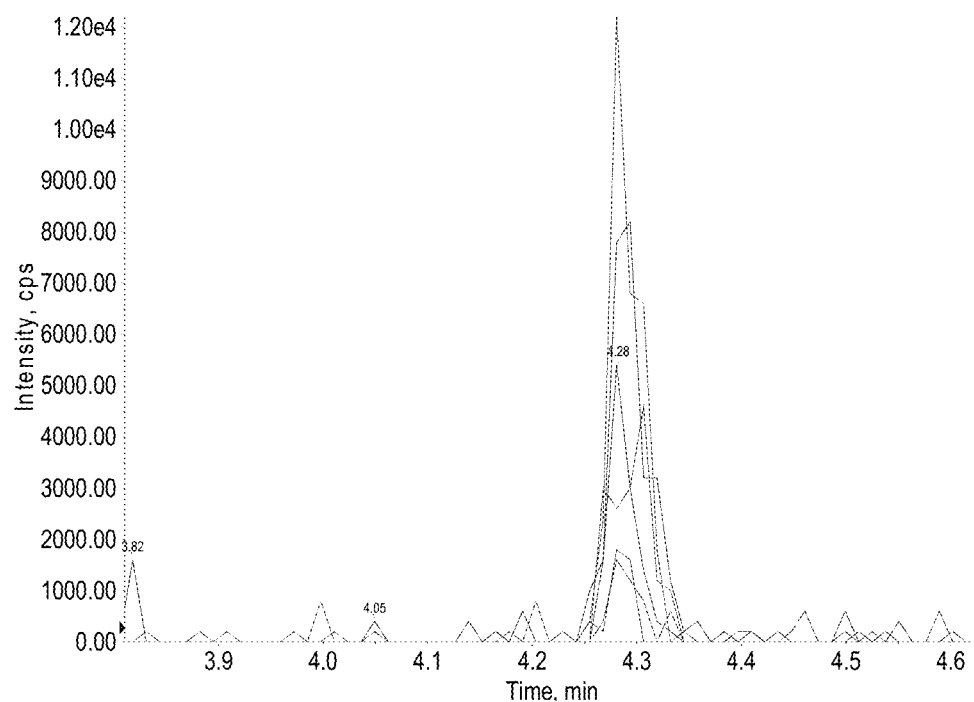
Figure 4B:
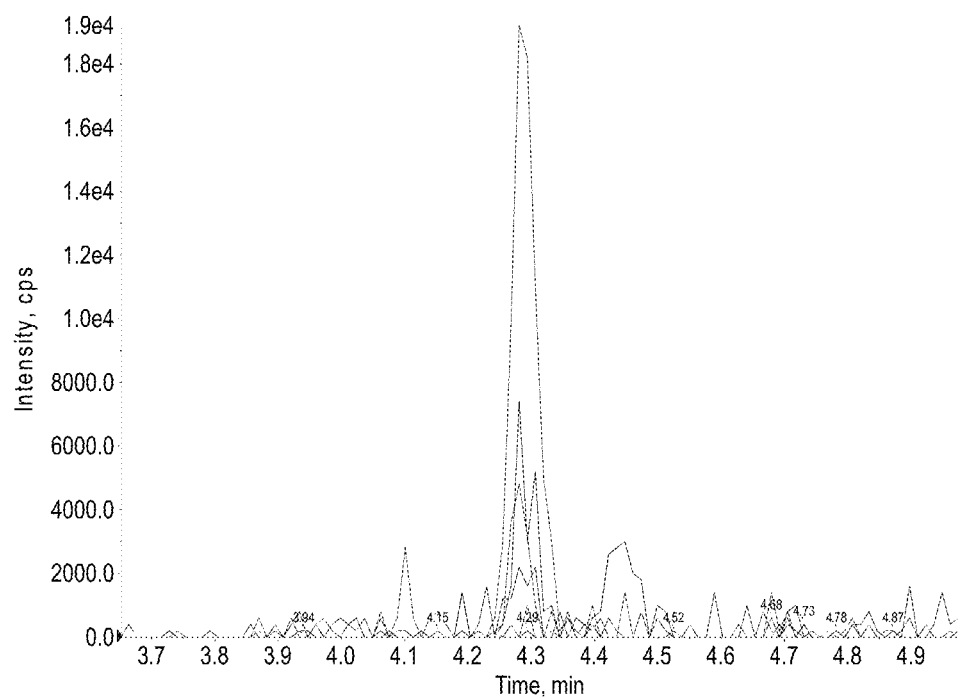
Figure 5:
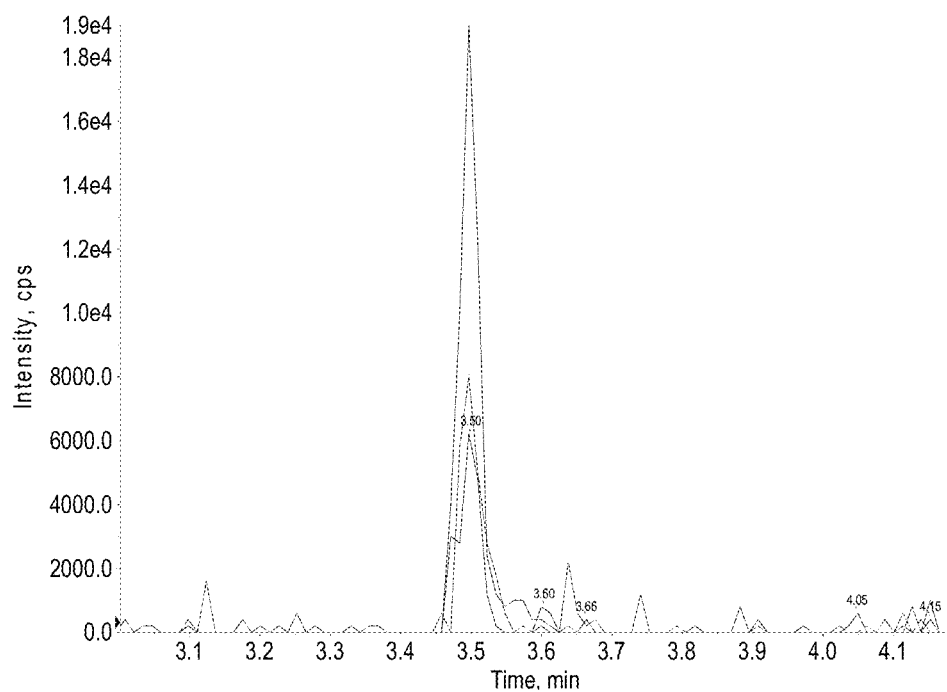
Figure 6:
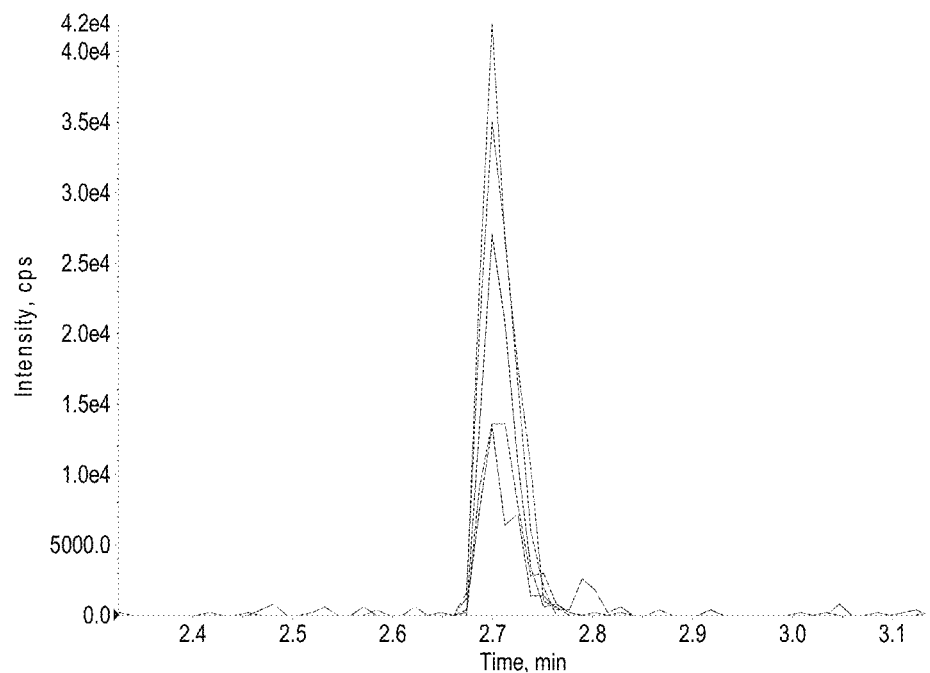
Figure 7:
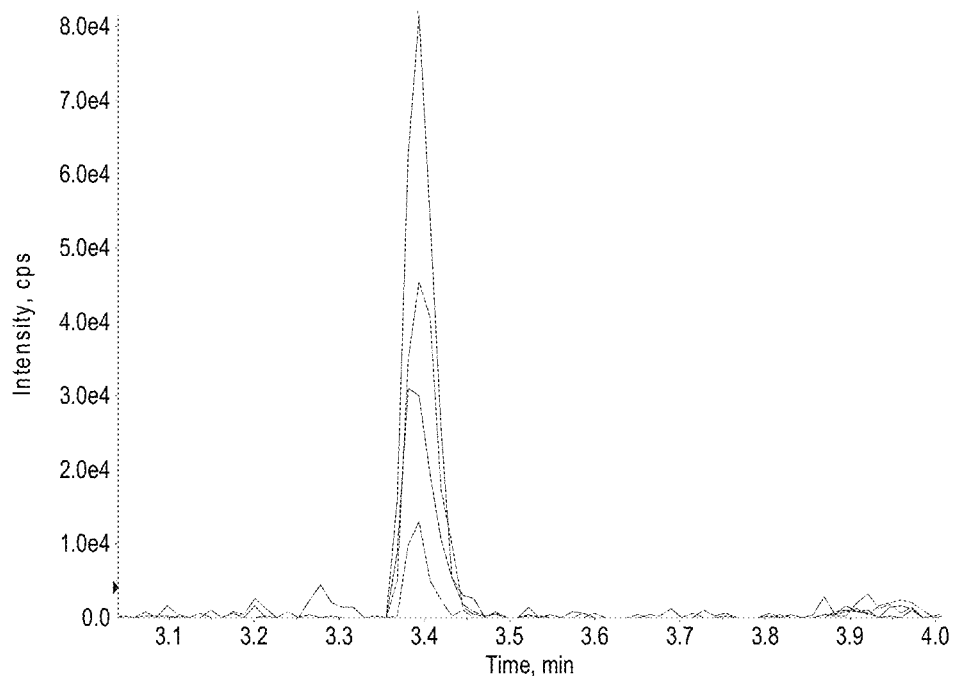
Figure 8:
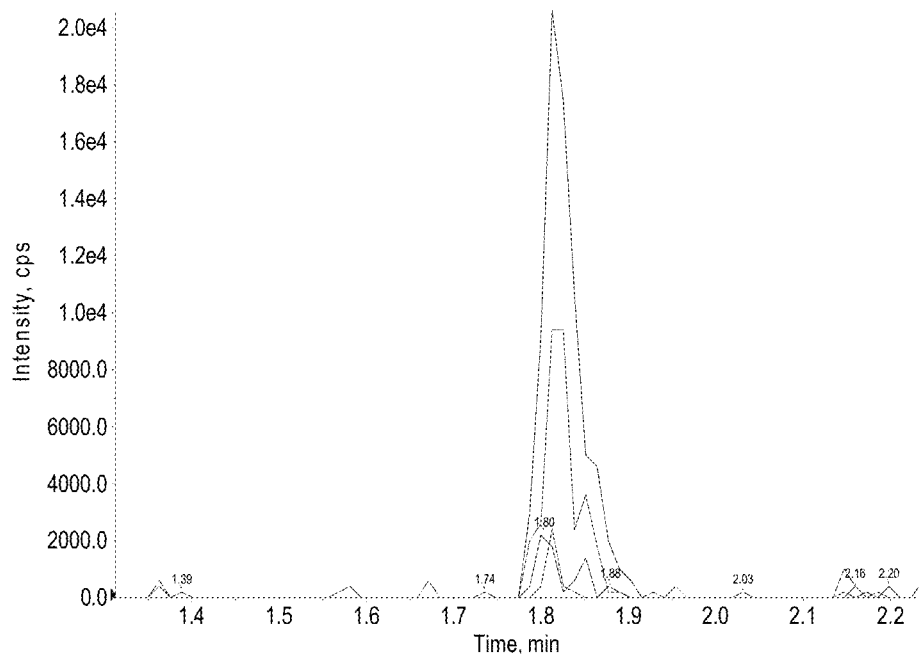
Figure 9:
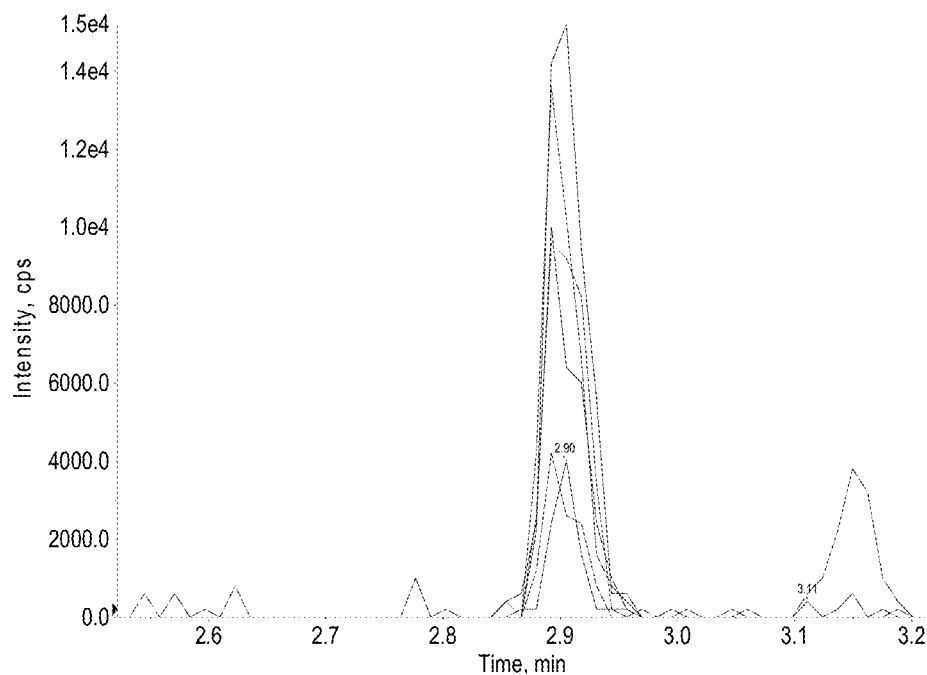
Figure 10:
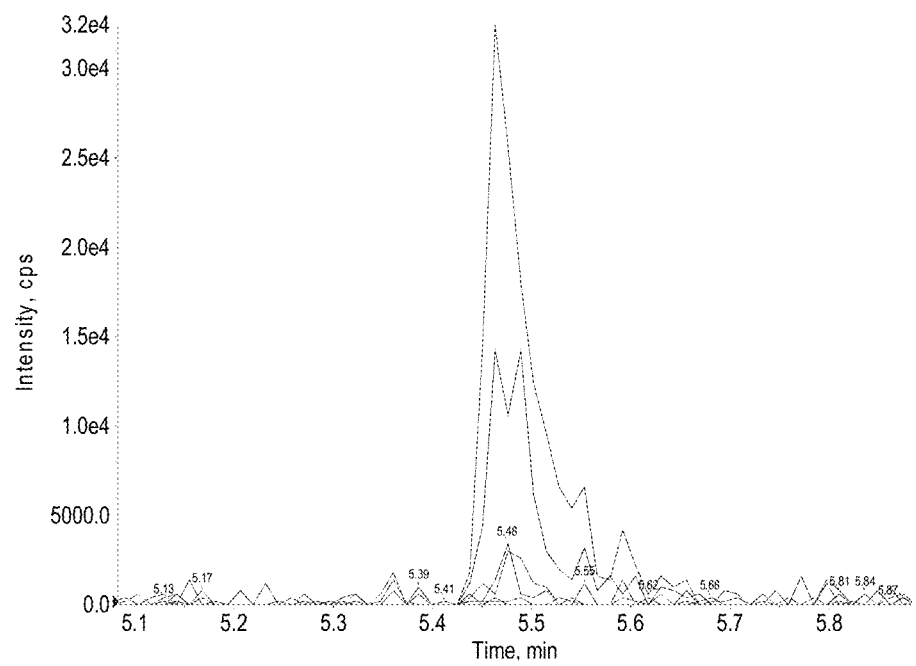
Figure 11:
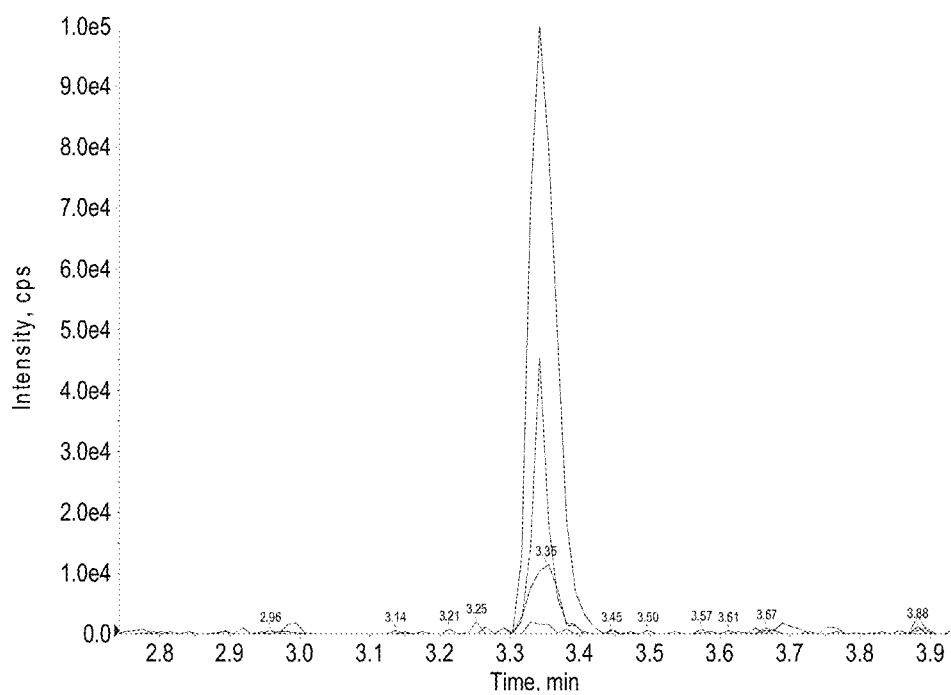
Figure 12:
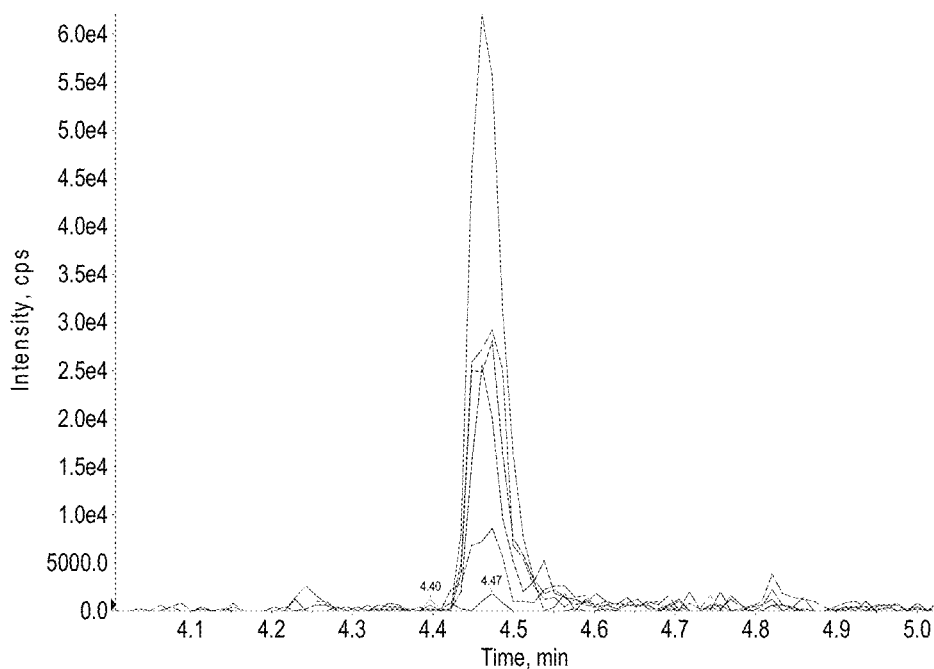
Figure 13:
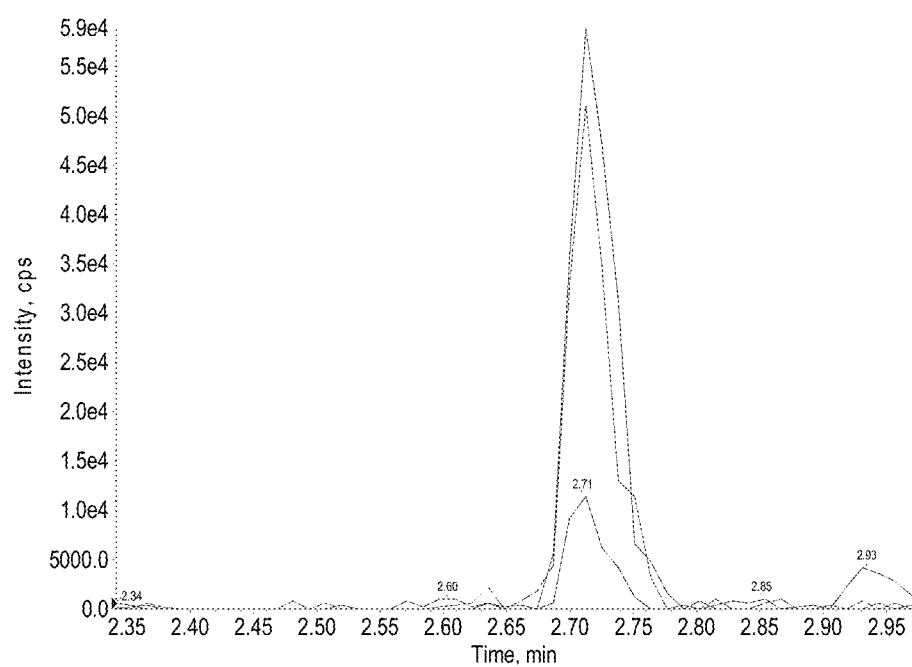

The selected signature peptides can be used for both qualitative and quantitative analysis of Gly m 7, either by itself or in combination with additional proteins in a multiplexing assay format. In this example, twelve signature peptides are selected from all peptide possibilities (SEQ ID NO: 32 AAELASMSAGAVK; SEQ ID NO: 33 AMGDIGGR; SEQ ID NO: 34 DTPQGSIEALQAGER, SEQ ID NO: 35 DYTLQAAEK, SEQ ID NO: 36 GLAASAGETAK, SEQ ID NO: 37 QSWLETR, SEQ ID NO: 38 SAAGYAAK, SEQ ID NO: 39 SAGGTTASYVGEK, SEQ ID NO: 40 SAWEQISNYSDQATQGVK, SEQ ID NO: 41 SLTSIGEK, SEQ ID NO: 42 TTAVITCTLEK, and SEQ ID NO: 43 VAADLR), and representative quantitation of these signature peptides are shown in FIGS. 2-13. Synthetic peptides can directly serve as an analytical reference standard for protein quantitation.

I claim:

1. A method of selecting candidate signature peptide for quantitation of known allergen and potential allergens from a plant-based sample, wherein the potential allergens comprise at least one sequence selected from SEQ ID NOs: 13-15, comprising:
   (a) identifying potential allergens based on homology to at least one known allergen protein sequence, wherein the at least one known allergen comprises Gly m 7 and the identified potential allergens comprise at least one sequence selected from the group consisting of SEQ ID NO:13, SEQ ID NO:14, and SEQ ID NO:15;
   (b) performing sequence alignment of the at least one known allergen and potential allergens identified in step (a);
   (c) selecting a consensus sequence or representative sequence based on the sequence alignment;
   (d) determining a plural of candidate signature peptides based on conservative regions or domains from the sequence alignment and in silico digestion data of the consensus sequence or representative sequence selected in Step (c); and
   (e) quantitating the amount of the at least one known allergen and potential allergens in the plant-based sample based on measurements of the signature peptides.

2. The method of claim 1, wherein the quantitating step uses a column chromatography and mass spectrometry.

3. The method of claim 1, wherein the quantitating step comprises measuring the plural of candidate signature peptides using high resolution accurate mass spectrometry (HRAM MS).

4. The method of claim 1, wherein the quantitating step comprises calculating corresponding peak heights or peak areas of the candidate signature peptides from mass spectrometry.

5. The method of claim 1, wherein the quantitating step comprises comparing data from high fragmentation mode and low fragmentation mode from mass spectrometry.

6. The method of claim 1, wherein the at least one known allergen comprises Gly m 7.

7. The method of claim 1, wherein the candidate signature peptides comprise at least one sequence selected from SEQ ID NOs: 33-43.

8. The method of claim 1, wherein the candidate signature peptides comprise SEQ ID NO: 33, 37, or 41.

9. The method of claim 1, wherein the plant-based sample comprises a soybean seed or part of a soybean seed.

* * * * *